United States Patent [19]
Brenner et al.

[11] Patent Number: 5,714,330
[45] Date of Patent: *Feb. 3, 1998

[54] DNA SEQUENCING BY STEPWISE LIGATION AND CLEAVAGE

[75] Inventors: Sydney Brenner, Cambridge, England; Robert B. DuBridge, Belmont, Calif.

[73] Assignee: Lynx Therapeutics, Inc., Hayward, Calif.

[*] Notice: The term of this patent shall not extend beyond the expiration date of Pat. Nos. 5,552,278 and 5,599,675.

[21] Appl. No.: 667,689

[22] Filed: Jun. 21, 1996

Related U.S. Application Data

[63] Continuation-in-part of Ser. No. 410,116, Mar. 24, 1995, Pat. No. 5,599,675, which is a continuation-in-part of Ser. No. 280,441, Jul. 25, 1994, Pat. No. 5,552,278, which is a continuation-in-part of Ser. No. 222,300, Apr. 4, 1994, abandoned.

[51] Int. Cl.$^6$ .............. C12Q 1/68; C12P 19/34; C07H 21/04; C07H 21/02
[52] U.S. Cl. .............. 435/6; 435/91.1; 435/91.2; 435/91.52; 435/91.53; 536/24.3; 935/77; 935/78
[58] Field of Search .............. 435/6, 91.1, 91.2, 435/91.52, 91.53; 536/24.3; 935/77, 78

[56] References Cited

U.S. PATENT DOCUMENTS

| | | | |
|---|---|---|---|
| 4,237,224 | 12/1980 | Cohen | 435/68 |
| 4,293,652 | 10/1981 | Cohen | 435/172 |
| 4,321,365 | 3/1982 | Wu et al. | 536/27 |
| 4,683,202 | 7/1987 | Mullis | 435/91 |
| 4,775,619 | 10/1988 | Urdea | 435/6 |
| 5,093,245 | 3/1992 | Keith et al. | 435/91 |
| 5,102,785 | 4/1992 | Livak et al. | 435/6 |
| 5,118,605 | 6/1992 | Urdea | 435/6 |
| 5,126,239 | 6/1992 | Livak et al. | 435/6 |
| 5,242,794 | 9/1993 | Whiteley et al. | 435/6 |
| 5,403,708 | 4/1995 | Brennan et al. | 435/6 |
| 5,508,169 | 4/1996 | Deugau et al. | 435/6 |
| 5,552,278 | 9/1996 | Brenner | 435/6 |
| 5,599,675 | 2/1997 | Brenner | 435/6 |

FOREIGN PATENT DOCUMENTS

| | | |
|---|---|---|
| 0 246 864 B1 | 11/1987 | European Pat. Off. . |
| 0 392 546 A2 | 10/1990 | European Pat. Off. . |
| 0 520 039 B1 | 12/1992 | European Pat. Off. . |
| 2 687 851 | 5/1994 | France . |
| WO92/15712 | 9/1992 | WIPO . |
| WO94/01582 | 1/1994 | WIPO . |
| WO95/20053 | 7/1995 | WIPO . |

OTHER PUBLICATIONS

Brenner and Livak, "DNA fingerprinting by sampled sequencing," Proc. Natl. Acad. Sci., 86: 8902–8906 (1989).

Carrano et al., "A high-resolution, fluorescence-based, semi-automated method for DNA fingerprinting," Genomics, 4: 129–136 (1989).

Szybalski et al, "Class-IIS restriction enzymes—a review," Gene, 100: 13–26 (1991).

(List continued on next page.)

*Primary Examiner*—W. Gary Jones
*Assistant Examiner*—Paul B. Tran
*Attorney, Agent, or Firm*—Stephen C. Macevicz

[57] ABSTRACT

The invention provides a method of nucleic acid sequence analysis based on repeated cycles of ligation to and cleavage of probes at the terminus of a target polynucleotide. At each such cycle one or more terminal nucleotides are identified and one or more nucleotides are removed from the end of the target polynucleotide, such that further cycles of ligation and cleavage can take place. At each cycle the target sequence is shortened by one or more nucleotides until the nucleotide sequence of the target polynucleotide is determined. The method obviates electrophoretic separation of similarly sized DNA fragments and eliminates the difficulties associated with the detection and analysis of spatially overlapping bands of DNA fragments in a gel, or like medium. The invention further obviates the need to generate DNA fragments from long single stranded templates with a DNA polymerase.

28 Claims, 18 Drawing Sheets

OTHER PUBLICATIONS

Kim et al, "Cleaving DNA at any predetermined site with adapter–primers and Class–IIS restriction enzymes," Science, 240:504–506 (1988).

Szybalski, "Universal restriction endonucleases: designing novel cleavage specificities by combining adapter oligonucleotide and enzyme moieties," Gene, 40: 169–173 (1985).

Barany, "The ligase chain reaction in a PCR world," PCR Methods and Applications, 1: 5–16 (1991).

Wu and Wallace, "The ligase amplification reaction (LAR)—amplification of specific DNA sequences using sequential rounds of template–dependent ligation," Genomics, 4:560–569 (1989).

McGuigan et al, "DNA fingerprinting by sampled sequencing," Methods in Enzymology, 218: 241–258 (1993).

Nelson et al, "Effect of site–specific methylation on restriction endonucleases and DNA modification methyltransferases," Nucleic Acids Research, 21: 3139–3154 (1993).

Roberts and Macelis, "REBASE—restriction enzymes and methylases," Nucleic Acids Research, 21: 3125–3137 (1993).

Syvanen et al, "A primer–guided nucleotide incorporation assay in the genotyping of apolipoprotein E," Genomics 8: 684–692 (1990).

Broude et al, "Enhanced DNA sequencing by hybridization," Proc. Natl. Acad. Sci., 91: 3072–3076 (1994).

Hultman et al, "Direct solid phase sequencing of genomic and plasmid DNA using magnetic beads as solid support," Nucleic Acids Research, 17: 4937–4946 (1989).

Loakes et al, "5–Niroindole as an universal base analogue," Nucleic Acids Research, 22: 4039–4043 (1994).

Nichols et al, "A universal nucleoside for use at ambiguous sites in DNA primers," Nature, 369: 492–493 (1994).

Nikiforov et al, "Genetic bit analysis: a solid phase method for typing single nucleotide polymorphisms," Nucleic Acids Research, 22: 4167–4175 (1994).

Berger, "Expanding the potential of restriction endonucleases: use of hapaxoterministic enzymes," Anal. Biochem., 222: 1–8 (1994).

Unrau et al, "Non–coding amplification of specific DNA fragments from whole genomic DNA digests using DNA 'indexers,'" Gene, 145: 163–169 (1994).

Syvanen et al, "Convenient and quantitative determination of the frequency of a mutant allele using solid–phase minisequencing: application to aspartyglucosaminuria in Finland," Genomics, 12: 590–595 (1992).

Wiaderkiewicz et al, "Mismatch and blunt to protruding end joining by DNA ligases," Nucleic Acids Research, 15: 7831–7848 (1987).

Tsiapalis et al, "On the fidelity of phage T4–induced polynucleotide ligase in the joining of chemically synthesized deoxyribooligonucleotides," Biochem. Biophys. Res. Comm., 39:631–636 (1970).

Goffin et al, "Nicks 3' or 5' to AP sites or to mispaired bases, and one–nucleotide gaps can be sealed by T4 DNA ligase," Nucleic Acids Research, 15: 8755–8771 (1987).

Ju et al, "Energy transfer primers: a new fluorescence labeling paradigm for DNA sequencing and analysis," Nature Medicine, 2: 246–249 (1996).

Ju et al, "Fluorescence energy transfer dye–labeled primers for DNA sequencing and analysis," Proc. Natl. Acad. Sci., 92: 4347–4351 (1995).

SEQUENCE LISTING ( 1 ) GENERAL INFORMATION:

( i i i ) NUMBER OF SEQUENCES: 41

( 2 ) INFORMATION FOR SEQ ID NO: 1:

( i ) SEQUENCE CHARACTERISTICS:
        ( A ) LENGTH: 18 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 1:

AGTGAATTCG AGCTCGGT                                              1 8

( 2 ) INFORMATION FOR SEQ ID NO: 2:

( i ) SEQUENCE CHARACTERISTICS:
        ( A ) LENGTH: 18 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 2:

CCTTTGAGTG AGCTGATA                                              1 8

( 2 ) INFORMATION FOR SEQ ID NO: 3:

( i ) SEQUENCE CHARACTERISTICS:
        ( A ) LENGTH: 30 nucleotides
        ( B ) TYPE: nucleic acid
        ( C ) STRANDEDNESS: double
        ( D ) TOPOLOGY: linear ( x i ) SEQUENCE DESCRIPTION: SEQ ID NO: 3:

AATTCGAGCT CGGTACCCGG GGATCCTCTA                            3 0

( 2 ) INFORMATION FOR SEQ ID NO: 4:

( i ) SEQUENCE CHARACTERISTICS:
        ( A ) LENGTH: 26 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 4:

TAGAGGATCC CCGGGTACCG AGCTCG                                  2 6

( 2 ) INFORMATION FOR SEQ ID NO: 5:

( i ) SEQUENCE CHARACTERISTICS:

(A) LENGTH: 16 nucleotides
        (B) TYPE: nucleic acid
        (C) STRANDEDNESS: single
        (D) TOPOLOGY: linear (xi) SEQUENCE DESCRIPTION: SEQ ID NO: 5:

ATCGGATGAC ATCAAC            16

(2) INFORMATION FOR SEQ ID NO: 6:

(i) SEQUENCE CHARACTERISTICS:
        (A) LENGTH: 20 nucleotides
        (B) TYPE: nucleic acid
        (C) STRANDEDNESS: single
        (D) TOPOLOGY: linear (xi) SEQUENCE DESCRIPTION: SEQ ID NO: 6:

NNNAGTTGAT GTCATCCGAT            20

(2) INFORMATION FOR SEQ ID NO: 7:

(i) SEQUENCE CHARACTERISTICS:
        (A) LENGTH: 20 nucleotides
        (B) TYPE: nucleic acid
        (C) STRANDEDNESS: single
        (D) TOPOLOGY: linear (xi) SEQUENCE DESCRIPTION: SEQ ID NO: 7:

NNNCGTTGAT GTCATCCGAT            20

(2) INFORMATION FOR SEQ ID NO: 8:

(i) SEQUENCE CHARACTERISTICS:
        (A) LENGTH: 20 nucleotides
        (B) TYPE: nucleic acid
        (C) STRANDEDNESS: single
        (D) TOPOLOGY: linear (xi) SEQUENCE DESCRIPTION: SEQ ID NO: 8:

NNNGGTTGAT GTCATCCGAT            20

(2) INFORMATION FOR SEQ ID NO: 9:

(i) SEQUENCE CHARACTERISTICS:
        (A) LENGTH: 20 nucleotides
        (B) TYPE: nucleic acid
        (C) STRANDEDNESS: single
        (D) TOPOLOGY: linear (xi) SEQUENCE DESCRIPTION: SEQ ID NO: 9:

NNNTGTTGAT GTCATCCGAT            20

(2) INFORMATION FOR SEQ ID NO: 10:

(i) SEQUENCE CHARACTERISTICS:
        (A) LENGTH: 11 nucleotides
        (B) TYPE: nucleic acid
        (C) STRANDEDNESS: single
        (D) TOPOLOGY: linear (xi) SEQUENCE DESCRIPTION: SEQ ID NO: 10:

NNNNGAACAG T            11

(2) INFORMATION FOR SEQ ID NO: 11:

(i) SEQUENCE CHARACTERISTICS:
        (A) LENGTH: 10 nucleotides
        (B) TYPE: nucleic acid ( C ) STRANDEDNESS: single
            ( D ) TOPOLOGY: linear ( x i ) SEQUENCE DESCRIPTION: SEQ ID NO: 11:

NNNNTACCGG                                                                         10

( 2 ) INFORMATION FOR SEQ ID NO: 12:

( i ) SEQUENCE CHARACTERISTICS:
            ( A ) LENGTH: 17 nucleotides
            ( B ) TYPE: nucleic acid
            ( C ) STRANDEDNESS: double
            ( D ) TOPOLOGY: linear ( x i ) SEQUENCE DESCRIPTION: SEQ ID NO: 12:

ACTCTTCNNN NTACCGG                                                                 17

( 2 ) INFORMATION FOR SEQ ID NO: 13:

( i ) SEQUENCE CHARACTERISTICS:
            ( A ) LENGTH: 11 nucleotides
            ( B ) TYPE: nucleic acid
            ( C ) STRANDEDNESS: double
            ( D ) TOPOLOGY: linear ( x i ) SEQUENCE DESCRIPTION: SEQ ID NO: 13:

NNNNGAACAG T                                                                       11

( 2 ) INFORMATION FOR SEQ ID NO: 14:

( i ) SEQUENCE CHARACTERISTICS:
            ( A ) LENGTH: 12 nucleotides
            ( B ) TYPE: nucleic acid
            ( C ) STRANDEDNESS: single
            ( D ) TOPOLOGY: linear ( x i ) SEQUENCE DESCRIPTION: SEQ ID NO: 14:

AGACGCCATC AT                                                                      12

( 2 ) INFORMATION FOR SEQ ID NO: 15:

( i ) SEQUENCE CHARACTERISTICS:
            ( A ) LENGTH: 16 nucleotides
            ( B ) TYPE: nucleic acid
            ( C ) STRANDEDNESS: single
            ( D ) TOPOLOGY: linear ( x i ) SEQUENCE DESCRIPTION: SEQ ID NO: 15:

NNNNATGATG GCGTCT                                                                  16

( 2 ) INFORMATION FOR SEQ ID NO: 16:

( i ) SEQUENCE CHARACTERISTICS:
            ( A ) LENGTH: 10 nucleotides
            ( B ) TYPE: nucleic acid
            ( C ) STRANDEDNESS: single
            ( D ) TOPOLOGY: linear ( x i ) SEQUENCE DESCRIPTION: SEQ ID NO: 16:

NNNNTACCGG                                                                         10

( 2 ) INFORMATION FOR SEQ ID NO: 17:

( i ) SEQUENCE CHARACTERISTICS:
            ( A ) LENGTH: 22 nucleotides
            ( B ) TYPE: nucleic acid
            ( C ) STRANDEDNESS: double
            ( D ) TOPOLOGY: linear (xi) SEQUENCE DESCRIPTION: SEQ ID NO: 17:

AGACGCCATC ATNNNNTACC GG    22

(2) INFORMATION FOR SEQ ID NO: 18:

(i) SEQUENCE CHARACTERISTICS:
        (A) LENGTH: 11 nucleotides
        (B) TYPE: nucleic acid
        (C) STRANDEDNESS: single
        (D) TOPOLOGY: linear (xi) SEQUENCE DESCRIPTION: SEQ ID NO: 18:

TNNNNTACCG G    11

(2) INFORMATION FOR SEQ ID NO: 19:

(i) SEQUENCE CHARACTERISTICS:
        (A) LENGTH: 11 nucleotides
        (B) TYPE: nucleic acid
        (C) STRANDEDNESS: single
        (D) TOPOLOGY: linear (xi) SEQUENCE DESCRIPTION: SEQ ID NO: 19:

AGACGCCATC A    11

(2) INFORMATION FOR SEQ ID NO: 20:

(i) SEQUENCE CHARACTERISTICS:
        (A) LENGTH: 16 nucleotides
        (B) TYPE: nucleic acid
        (C) STRANDEDNESS: single
        (D) TOPOLOGY: linear (xi) SEQUENCE DESCRIPTION: SEQ ID NO: 20:

NNNNATGATG GCGTCT    16

(2) INFORMATION FOR SEQ ID NO: 21:

(i) SEQUENCE CHARACTERISTICS:
        (A) LENGTH: 10 nucleotides
        (B) TYPE: nucleic acid
        (C) STRANDEDNESS: single
        (D) TOPOLOGY: linear (xi) SEQUENCE DESCRIPTION: SEQ ID NO: 21:

ACTCTTCGNN    10

(2) INFORMATION FOR SEQ ID NO: 22:

(i) SEQUENCE CHARACTERISTICS:
        (A) LENGTH: 16 nucleotides
        (B) TYPE: nucleic acid
        (C) STRANDEDNESS: double
        (D) TOPOLOGY: linear (xi) SEQUENCE DESCRIPTION: SEQ ID NO: 22:

ACTCTTCGNN TACCGG    16

(2) INFORMATION FOR SEQ ID NO: 23:

(i) SEQUENCE CHARACTERISTICS:
        (A) LENGTH: 12 nucleotides
        (B) TYPE: nucleic acid
        (C) STRANDEDNESS: single
        (D) TOPOLOGY: linear (xi) SEQUENCE DESCRIPTION: SEQ ID NO: 23:

NNNNCATCCG AT                                                                    12

( 2 ) INFORMATION FOR SEQ ID NO: 24:

( i ) SEQUENCE CHARACTERISTICS:
        ( A ) LENGTH: 13 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 24:

CAGATCCTCT TCA                                                                   13

( 2 ) INFORMATION FOR SEQ ID NO: 25:

( i ) SEQUENCE CHARACTERISTICS:
        ( A ) LENGTH: 17 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 25:

NNNNTGAACA GGATCTG                                                               17

( 2 ) INFORMATION FOR SEQ ID NO: 26:

( i ) SEQUENCE CHARACTERISTICS:
        ( A ) LENGTH: 12 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 26:

CAGATCCTCT TC                                                                    12

( 2 ) INFORMATION FOR SEQ ID NO: 27:

( i ) SEQUENCE CHARACTERISTICS:
        ( A ) LENGTH: 15 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 27:

NNGGAAGAGG ATCTG                                                                 15

( 2 ) INFORMATION FOR SEQ ID NO: 28:

( i ) SEQUENCE CHARACTERISTICS:
        ( A ) LENGTH: 15 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 28:

NNCGAAGAGG ATCTG                                                                 15

( 2 ) INFORMATION FOR SEQ ID NO: 29:

( i ) SEQUENCE CHARACTERISTICS:
        ( A ) LENGTH: 15 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 29:

NNAGAAGAGG ATCTG                                                                 15

( 2 ) INFORMATION FOR SEQ ID NO: 30:

( i ) SEQUENCE CHARACTERISTICS:
        ( A ) LENGTH: 15 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 30:

NNTGAAGAGG ATCTG            15

( 2 ) INFORMATION FOR SEQ ID NO: 31:

( i ) SEQUENCE CHARACTERISTICS:
        ( A ) LENGTH: 34 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 31:

CTAAACCATT GGTATGGGCC AGTGAATTGT AATA        34

( 2 ) INFORMATION FOR SEQ ID NO: 32:

( i ) SEQUENCE CHARACTERISTICS:
        ( A ) LENGTH: 55 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 32:

CGCGCAGCCC GCATCGTTTA TGCTACAGAC TGTCAGTGCA        40

GCTCTCCGAT CCAAA            55

( 2 ) INFORMATION FOR SEQ ID NO: 33:

( i ) SEQUENCE CHARACTERISTICS:
        ( A ) LENGTH: 13 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 33:

TTTAAGCTAC AGA            13

( 2 ) INFORMATION FOR SEQ ID NO: 34:

( i ) SEQUENCE CHARACTERISTICS:
        ( A ) LENGTH: 18 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 34:

GCTCGGGATG CGCACGTA        18

( 2 ) INFORMATION FOR SEQ ID NO: 35:

( i ) SEQUENCE CHARACTERISTICS:
        ( A ) LENGTH: 24 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 35:

GNNNTACGTG CGCATCCCGA GCNA        24

( 2 ) INFORMATION FOR SEQ ID NO: 36:

( i ) SEQUENCE CHARACTERISTICS:
( A ) LENGTH: 24 nucleotides
( B ) TYPE: nucleic acid
( C ) STRANDEDNESS: single
( D ) TOPOLOGY: linear ( x i ) SEQUENCE DESCRIPTION: SEQ ID NO: 36:

TNNNTACGTG CGCATCCCGA GCNA    24

( 2 ) INFORMATION FOR SEQ ID NO: 37:

( i ) SEQUENCE CHARACTERISTICS:
( A ) LENGTH: 24 nucleotides
( B ) TYPE: nucleic acid
( C ) STRANDEDNESS: single
( D ) TOPOLOGY: linear ( x i ) SEQUENCE DESCRIPTION: SEQ ID NO: 37:

CNNNTACGTG CGCATCCCGA GCNA    24

( 2 ) INFORMATION FOR SEQ ID NO: 38:

( i ) SEQUENCE CHARACTERISTICS:
( A ) LENGTH: 24 nucleotides
( B ) TYPE: nucleic acid
( C ) STRANDEDNESS: single
( D ) TOPOLOGY: linear ( x i ) SEQUENCE DESCRIPTION: SEQ ID NO: 38:

ANNNTACGTG CGCATCCCGA GCNA    24

( 2 ) INFORMATION FOR SEQ ID NO: 39:

( i ) SEQUENCE CHARACTERISTICS:
( A ) LENGTH: 22 nucleotides
( B ) TYPE: nucleic acid
( C ) STRANDEDNESS: single
( D ) TOPOLOGY: linear ( x i ) SEQUENCE DESCRIPTION: SEQ ID NO: 39:

CCCGACGTCG CATGCTCCTC TA    22

( 2 ) INFORMATION FOR SEQ ID NO: 40:

( i ) SEQUENCE CHARACTERISTICS:
( A ) LENGTH: 20 nucleotides
( B ) TYPE: nucleic acid
( C ) STRANDEDNESS: single
( D ) TOPOLOGY: linear ( x i ) SEQUENCE DESCRIPTION: SEQ ID NO: 40:

GCGCGTTGGC CGATTCATTA    20

( 2 ) INFORMATION FOR SEQ ID NO: 41:

( i ) SEQUENCE CHARACTERISTICS:
( A ) LENGTH: 15 nucleotides
( B ) TYPE: nucleic acid
( C ) STRANDEDNESS: double
( D ) TOPOLOGY: linear ( x i ) SEQUENCE DESCRIPTION: SEQ ID NO: 41:

NNGGATGNGA TATCN    15

DNA SEQUENCING BY STEPWISE LIGATION AND CLEAVAGE

This is a continuation-in-part of U.S. patent application Ser. No. 08/410,116 filed 24 Mar. 1995, now U.S. Pat. No. 5,599,675 which is a continuation-in-part of U.S. patent application Ser. No. 08/280,441 filed 25 Jul. 1994, now U.S. Pat. No. 5,552,278, which is a continuation-in-part of U.S. patent application Ser. No. 08/222,300 filed 4 Apr. 1994, now abandoned.

FIELD OF THE INVENTION

The invention relates generally to methods for determining the nucleotide sequence of a polynucleotide, and more particularly, to a method of step-wise removal and identification of terminal nucleotides of a polynucleotide.

BACKGROUND

Analysis of polynucleotides with currently available techniques provides a spectrum of information ranging from the confirmation that a test polynucleotide is the same or different than a standard sequence or an isolated fragment to the express identification and ordering of each nucleoside of the test polynucleotide. Not only are such techniques crucial for understanding the function and control of genes and for applying many of the basic techniques of molecular biology, but they have also become increasingly important as tools in genomic analysis and a great many non-research applications, such as genetic identification, forensic analysis, genetic counseling, medical diagnostics, and the like. In these latter applications both techniques providing partial sequence information, such as fingerprinting and sequence comparisons, and techniques providing full sequence determination have been employed, e.g. Gibbs et al, Proc. Natl. Acad. Sci., 86: 1919–1923 (1989); Gyllensten et al, Proc. Natl. Acad. Sci. 85: 7652–7656 (1988); Carrano et al, Genomics, 4: 129–136 (1989); Caetano-Anolles et al, Mol. Gen. Genet., 235: 157–165 (1992); Brenner and Livak, Proc. Natl. Acad. Sci., 86: 8902–8906 (1989); Green et al, PCR Methods and Applications, 1: 77–90 (1991); and Versalovic et al, Nucleic Acids Research, 19: 6823–6831 (1991).

Native DNA consists of two linear polymers, or strands of nucleotides. Each strand is a chain of nucleosides linked by phosphodiester bonds. The two strands are held together in an antiparallel orientation by hydrogen bonds between complementary bases of the nucleotides of the two strands: deoxyadenosine (A) pairs with thymidine (T) and deoxyguanosine (G) pairs with deoxycytidine (C).

Presently there are two basic approaches to DNA sequence determination: the dideoxy chain termination method, e.g. Sanger et al, Proc. Natl. Acad. Sci., 74: 5463–5467 (1977); and the chemical degradation method, e.g. Maxam et al, Proc. Natl. Acad. Sci., 74: 560–564 (1977). The chain termination method has been improved in several ways, and serves as the basis for all currently available automated DNA sequencing machines, e.g. Sanger et al, J. Mol. Biol., 143: 161–178 (1980); Schreier et al, J. Mol. Biol., 129: 169–172 (1979); Smith et al, Nucleic Acids Research, 13: 2399–2412 (1985); Smith et al, Nature, 321: 674–679 (1987); Prober et al, Science, 238: 336–341 (1987); Section II, Meth. Enzymol., 155: 51–334 (1987); Church et al, Science, 240: 185–188 (1988); Hunkapiller et al, Science, 254: 59–67 (1991); Bevan et al, PCR Methods and Applications, 1: 222–228 (1992).

Both the chain termination and chemical degradation methods require the generation of one or more sets of labeled DNA fragments, each having a common origin and each terminating with a known base. The set or sets of fragments must then be separated by size to obtain sequence information. In both methods, the DNA fragments are separated by high resolution gel electrophoresis, which must have the capacity of distinguishing very large fragments differing in size by no more than a single nucleotide. Unfortunately, this step severely limits the size of the DNA chain that can be sequenced at one time. Sequencing using these techniques can reliably accommodate a DNA chain of up to about 400–450 nucleotides, Bankier et al, Meth. Enzymol., 155: 51–93 (1987); and Hawkins et al, Electrophoresis, 13: 552–559 (1992).

Several significant technical problems have seriously impeded the application of such techniques to the sequencing of long target polynucleotides, e.g. in excess of 500–600 nucleotides, or to the sequencing of high volumes of many target polynucleotides. Such problems include i) the gel electrophoretic separation step which is labor intensive, is difficult to automate, and introduces an extra degree of variability in the analysis of data, e.g. band broadening due to temperature effects, compressions due to secondary structure in the DNA sequencing fragments, inhomogeneities in the separation gel, and the like; ii) nucleic acid polymerases whose properties, such as processivity, fidelity, rate of polymerization, rate of incorporation of chain terminators, and the like, are often sequence dependent; iii) detection and analysis of DNA sequencing fragments which are typically present in fmol quantities in spatially overlapping bands in a gel; iv) lower signals because the labeling moiety is distributed over the many hundred spatially separated bands rather than being concentrated in a single homogeneous phase, and v) in the case of single-lane fluorescence detection, the availability of dyes with suitable emission and absorption properties, quantum yield, and spectral resolvability, e.g. Trainor, Anal. Biochem., 62: 418–426 (1990); Connell et al, Biotechniques, 5: 342–348 (1987); Karger et al, Nucleic Acids Research, 19: 4955–4962 (1991); Fung et al, U.S. Pat. No. 4,855,225; and Nishikawa et al, Electrophoresis, 12: 623–631 (1991).

Another problem exists with current technology in the area of diagnostic sequencing. An ever widening array of disorders, susceptibilities to disorders, prognoses of disease conditions, and the like, have been correlated with the presence of particular DNA sequences, or the degree of variation (or mutation) in DNA sequences, at one or more genetic loci. Examples of such phenomena include human leukocyte antigen (HLA) typing, cystic fibrosis, tumor progression and heterogeneity, p53 proto-oncogene mutations, ras proto-oncogene mutations, and the like, e.g. Gyllensten et al, PCR Methods and Applications, 1: 91–98 (1991); Santamaria et al, International application PCT/US92/01675; Tsui et al, International application PCT/CA90/00267; and the like. A difficulty in determining DNA sequences associated with such conditions to obtain diagnostic or prognostic information is the frequent presence of multiple subpopulations of DNA, e.g. allelic variants, multiple mutant forms, and the like. Distinguishing the presence and identity of multiple sequences with current sequencing technology is virtually impossible, without additional work to isolate and perhaps clone the separate species of DNA.

A major advance in sequencing technology could be made if an alternative approach was available for sequencing DNA that did not required high resolution separations, provided signals more amenable to analysis, and provided a means for readily analyzing DNA from heterozygous genetic loci.

SUMMARY OF THE INVENTION

The invention provides a method of nucleic acid sequence analysis based on ligation and cleavage of probes at the terminus of a target polynucleotide. Preferably, repeated cycles of such ligation and cleavage are implemented in the method, and in each such cycle a nucleotide is identified at the end of the target polynucleotide and the target polynucleotide is shortened, such that further cycles of ligation, cleavage, and identification can take place. That is, preferably, in each cycle the target sequence is shortened by a single nucleotide and the cycles are repeated until the nucleotide sequence of the target polynucleotide is determined.

An important feature of the invention is the probe employed in the ligation and cleavage events. A probe of the invention is a double stranded polynucleotide which (i) contains a recognition site for a nuclease, and (ii) preferably has a protruding strand capable of forming a duplex with a complementary protruding strand of the target polynucleotide. At each cycle in the latter embodiment, only those probes whose protruding strands form perfectly matched duplexes with the protruding strand of the target polynucleotide are ligated to the end of the target polynucleotide to form a ligated complex. After removal of the unligated probe, a nuclease recognizing the probe cuts the ligated complex at a site one or more nucleotides from the ligation site along the target polynucleotide leaving an end, usually a protruding strand, capable of participating in the next cycle of ligation and cleavage. An important feature of the nuclease is that its recognition site be separate from its cleavage site. As is described more fully below, in the course of such cycles of ligation and cleavage, the terminal nucleotides of the target polynucleotide are identified.

In one aspect of the invention, more than one nucleotide at the terminus of a target polynucleotide can be identified and/or cleaved during each cycle of the method.

Generally, the method of the invention comprises the following steps: (a) ligating a probe to an end of the polynucleotide, the probe having a nuclease recognition site; (b) identifying one or more nucleotides at the end of the polynucleotide; (c) cleaving the polynucleotide with a nuclease recognizing the nuclease recognition site of the probe such that the polynucleotide is shortened by one or more nucleotides; and (d) repeating steps (a) through (c) until the nucleotide sequence of the polynucleotide is determined. As is described more fully below, the order of steps (a) through (c) may vary with different embodiments of the invention. For example, identifying the one or more nucleotides can be carried out either before or after cleavage of the ligated complex from the target polynucleotide. Likewise, ligating a probe to the end of the polynucleotide may follow the step of identifying in some preferred embodiments of the invention. Preferably, the method further includes a step of removing the unligated probe after the step of ligating.

Preferably, whenever natural protein endonucleases are employed as the nuclease, the method further includes a step of methylating the target polynucleotide at the start of a sequencing operation to prevent spurious cleavages at internal recognition sites fortuitously located in the target polynucleotide.

The present invention overcomes many of the deficiencies inherent to current methods of DNA sequencing: there is no requirement for the electrophoretic separation of closely-sized DNA fragments; no difficult-to-automate gel-based separations are required; no polymerases are required for generating nested sets of DNA sequencing fragments; detection and analysis are greatly simplified because signal-to-noise ratios are much more favorable on a nucleotide-by-nucleotide basis, permitting smaller sample sizes to be employed; and for fluorescent-based detection schemes, analysis is further simplified because fluorophores labeling different nucleotides may be separately detected in homogeneous solutions rather than in spatially overlapping bands.

The present invention is readily automated, both for small-scale serial operation and for large-scale parallel operation, wherein many target polynucleotides or many segments of a single target polynucleotide are sequenced simultaneously. Unlike present sequencing approaches, the progressive nature of the method-that is, determination of a sequence nucleotide-by-nucleotide—permits one to monitor the progress of the sequencing operation in real time which, in turn, permits the operation to be curtailed, or re-started, if difficulties arise, thereby leading to significant savings in time and reagent usage. Also unlike current approaches, the method permits the simultaneous determination of allelic forms of a target polynucleotide: As described more fully below, if a population of target polynucleotides consists of several subpopulations of distinct sequences, e.g. polynucleotides from a heterozygous genetic locus, then the method can identify the proportion of each nucleotide at each position in the sequence.

Generally, the method of the invention is applicable to all tasks where DNA sequencing is employed, including medical diagnostics, genetic mapping, genetic identification, forensic analysis, molecular biology research, and the like.

DEFINITIONS

Figure 1A:
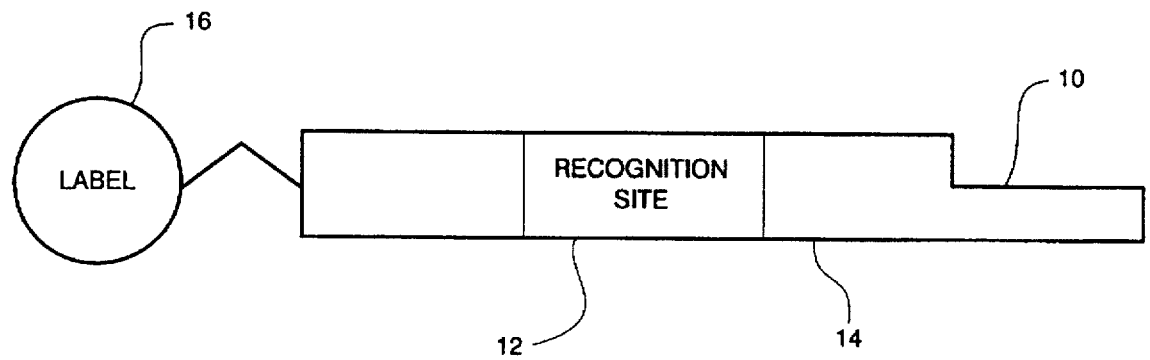
FIG. 1a illustrates a preferred structure of a labeled probe of the invention.

As used herein "sequence determination" or "determining a nucleotide sequence" in reference to polynucleotides includes determination of partial as well as full sequence information of the polynucleotide. That is, the term includes sequence comparisons, fingerprinting, and like levels of information about a target polynucleotide, as well as the express identification and ordering of nucleosides, usually each nucleoside, in a target polynucleotide. The term also includes the determination of the identification, ordering, and locations of one, two, or three of the four types of nucleotides within a target polynucleotide. For example, in some embodiments sequence identification may be effected by identifying the ordering and locations of a single type of nucleotide, e.g. cytosines, within a target polynucleotide so that its sequence is represented as a binary code, e.g. "100101 . . . " for "C-(not C)-(not C)-C-(not C)-C . . . " and the like.

"Perfectly matched duplex" in reference to the protruding strands of probes and target polynucleotides means that the protruding strand from one forms a double stranded structure with the other such that each nucleotide in the double stranded structure undergoes Watson-Crick base pairing with a nucleotide on the opposite strand. The term also comprehends the pairing of nucleoside analogs, such as deoxyinosine, nucleosides with 2-aminopurine bases, and the like, that may be employed to reduce the degeneracy of the probes.

The term "oligonucleotide" as used herein includes linear oligomers of nucleosides or analogs thereof, including deoxyribonucleosides, ribonucleosides, and the like. Usually oligonucleotides range in size from a few monomeric units, e.g. 3-4, to several hundreds of monomeric units. Whenever an oligonucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted.

As used herein, "nucleoside" includes the natural nucleosides, including 2'-deoxy and 2'-hydroxyl forms, e.g. as described in Kornberg and Baker, DNA Replication, 2nd Ed. (Freeman, San Francisco, 1992). "Analogs" in reference to nucleosides includes synthetic nucleosides having modified base moieties and/or modified sugar moieties, e.g. described generally by Scheit, Nucleotide Analogs (John Wiley, New York, 1980). Such analogs include synthetic nucleosides designed to enhance binding properties, reduce degeneracy, increase specificity, and the like.

DETAILED DESCRIPTION OF THE INVENTION

The invention provides a method of sequencing nucleic acids which obviates electrophoretic separation of similarly sized DNA fragments and which eliminates the difficulties associated with the detection and analysis of spatially overlapping bands of DNA fragments in a gel or like medium. Moreover, the invention obviates the need to generate DNA fragments from long single stranded templates with a DNA polymerase.

Structure of Probes

As mentioned above an important feature of the invention are the probes ligated to the target polynucleotide. Generally, the probes of the invention provide a "platform" from which a nuclease cleaves the target polynucleotide to which probe is ligated. Probes of the invention can also provide a means for identifying or labeling a nucleotide at the end of the target polynucleotide. Probes do not necessarily provide both functions in every embodiment.

In one aspect of the invention, probes have the form illustrated in FIG. 1a. In this embodiment, probes are double stranded segments of DNA having a protruding strand at one end 10, at least one nuclease recognition site 12, and a spacer region 14 between the recognition site and the protruding end 10. Preferably, probes also include a label 16, which in this particular embodiment is illustrated at the end opposite of the protruding strand. The probes may be labeled by a variety of means and at a variety of locations, the only restriction being that the labeling means selected does not interfere with the ligation step or with the recognition of the probe by the nuclease.

In the above embodiment, whenever a nuclease leaves a 5' phosphate on the terminus of the target polynucleotide, it is sometimes desirable to remove it, e.g. by treatment with a standard phosphatase, prior to ligation. This prevents undesired ligation of one of the strands, when the protruding strands of the probe and target sequence fail to form a perfectly matched duplex. This is particularly problematic when a mismatch occurs precisely at the nucleotide position where identification is sought. Where such phosphatase treatment is employed, the "nick" remaining in the ligated complex after the initial ligation can be repaired by kinase treatment followed by a second ligation step.

Preferably, embodiments of the invention employing the above type of probe comprise the following steps: (a) ligating a probe to an end of the polynucleotide having a protruding strand to form a ligated complex, the probe having a complementary protruding strand to that of the polynucleotide and the probe having a nuclease recognition site; (b) identifying one or more nucleotides in the protruding strand of the polynucleotide, e.g. by the identity of the ligated probe; (c) cleaving the ligated complex with a nuclease; and (d) repeating steps (a) through (c) until the nucleotide sequence of the polynucleotide is determined. The step of identifying can take place either before or after the step of cleaving. Preferably, the one or more nucleotides in the protruding strand of the polynucleotide are identified prior to cleavage. In further preference, the method also includes a step of removing unligated probe from the ligated complex.

It is not critical whether protruding strand 10 of the probe is a 5' or 3' end. However, in this embodiment, it is important that the protruding strands of the target polynucleotide and probes be capable of forming perfectly matched duplexes to allow for specific ligation. If the protruding strands of the target polynucleotide and probe are different lengths the resulting gap can be filled in by a polymerase prior to ligation, e.g. as in "gap LCR" disclosed in Backman et al, European patent application 91100959.5. Such gap filling can be used as a means for identifying one or more nucleotides in the protruding strand of the target polynucleotide. Preferably, the number of nucleotides in the respective protruding strands are the same so that both strands of the probe and target polynucleotide are capable of being ligated without a filling step. Preferably, the protruding strand of the probe is from 2 to 6 nucleotides long. As indicated below, the greater the length of the protruding strand, the greater the complexity of the probe mixture that is applied to the target polynucleotide during each ligation and cleavage cycle.

In another aspect of the invention, the primary function of the probe is to provide a site for a nuclease to bind to the ligated complex so that the complex can be cleaved and the target polynucleotide shortened. In this aspect of the invention, identification of the nucleotides can take place separately from probe ligation and cleavage. This embodiment provides several advantages: First, sequence determination does not require that the protruding strand of the ligated probe be perfectly complementary to the protruding strand of the target polynucleotide, thereby permitting greater flexibility in the control of hybridization stringency. Second, one need not provide a fully degenerate set of probes based on the four natural nucleotides. So-called "wild card" nucleotides, or "degeneracy reducing analogs" can be provided to significantly reduce, or even eliminate, the complexity of the probe mixture employed in the ligation step, since specific binding is not critical to nucleotide identification in this embodiment. Third, if identification is not carried out via a labeling means on the probe, then probes designed for blunt end ligation may be employed with no need for using degenerate mixtures.

Preferably, this embodiment of the invention comprises the following steps: (a) providing a polynucleotide having a protruding strand; (b) identifying one or more nucleotides in the protruding strand by extending a 3' end of a strand with a nucleic acid polymerase, (c) ligating a probe to an end of the polynucleotide to form a ligated complex; (d) cleaving the ligated complex with a nuclease; and (e) repeating steps (a) through (d) until the nucleotide sequence of the polynucleotide is determined. Preferably, the target polynucleotide has a 3' recessed strand which is extended by the nucleic acid polymerase in the presence of chain-terminating nucleoside triphosphates, and the nuclease used produces a 3'-recessed strand and 5' protruding strand at the terminus of the target polynucleotide.

Figure 1B:
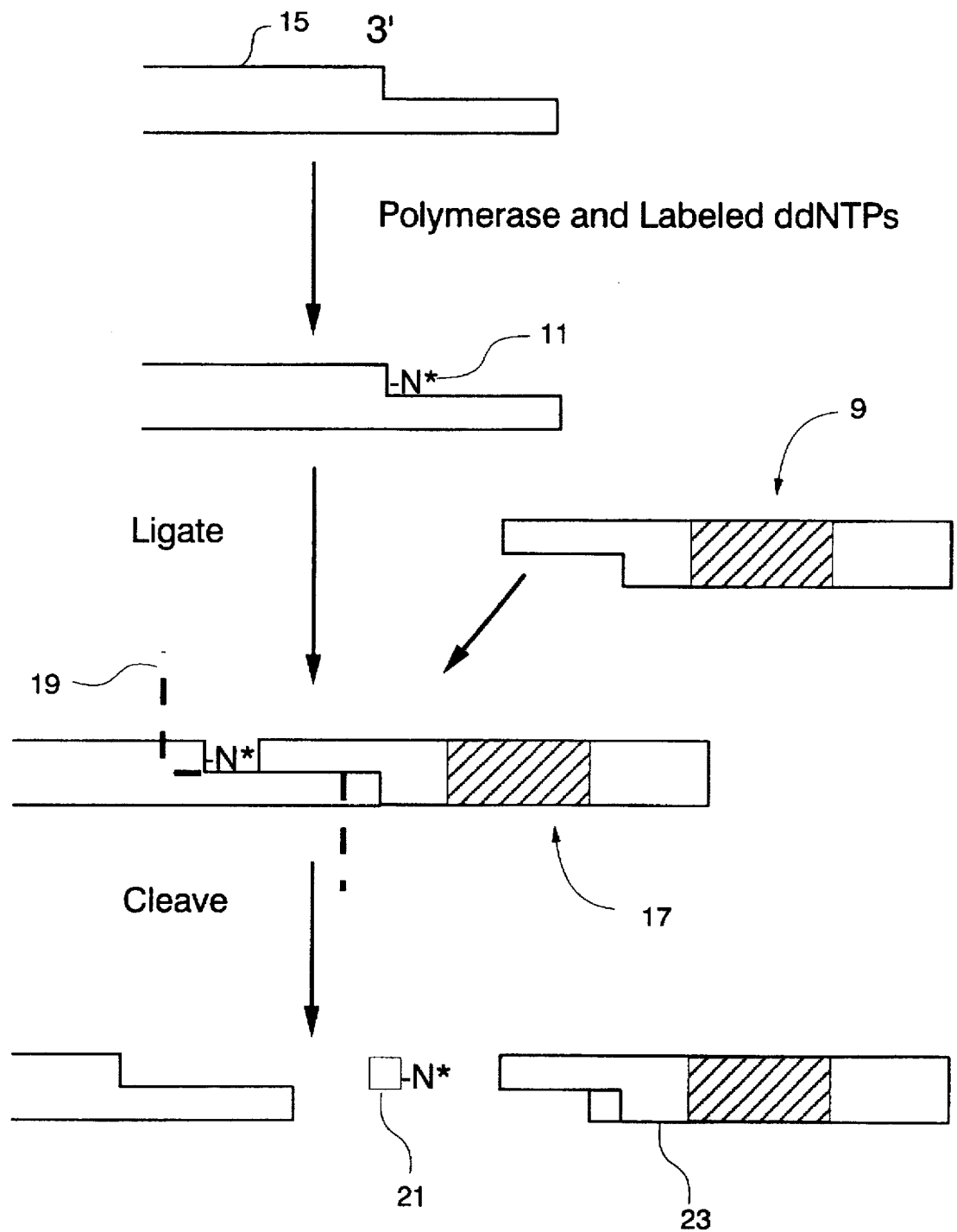
FIG. 1b illustrates a probe and terminus of a target polynucleotide wherein a separate labeling step is employed to identify one or more nucleotides in the protruding strand of a target polynucleotide.
Figure 1C:
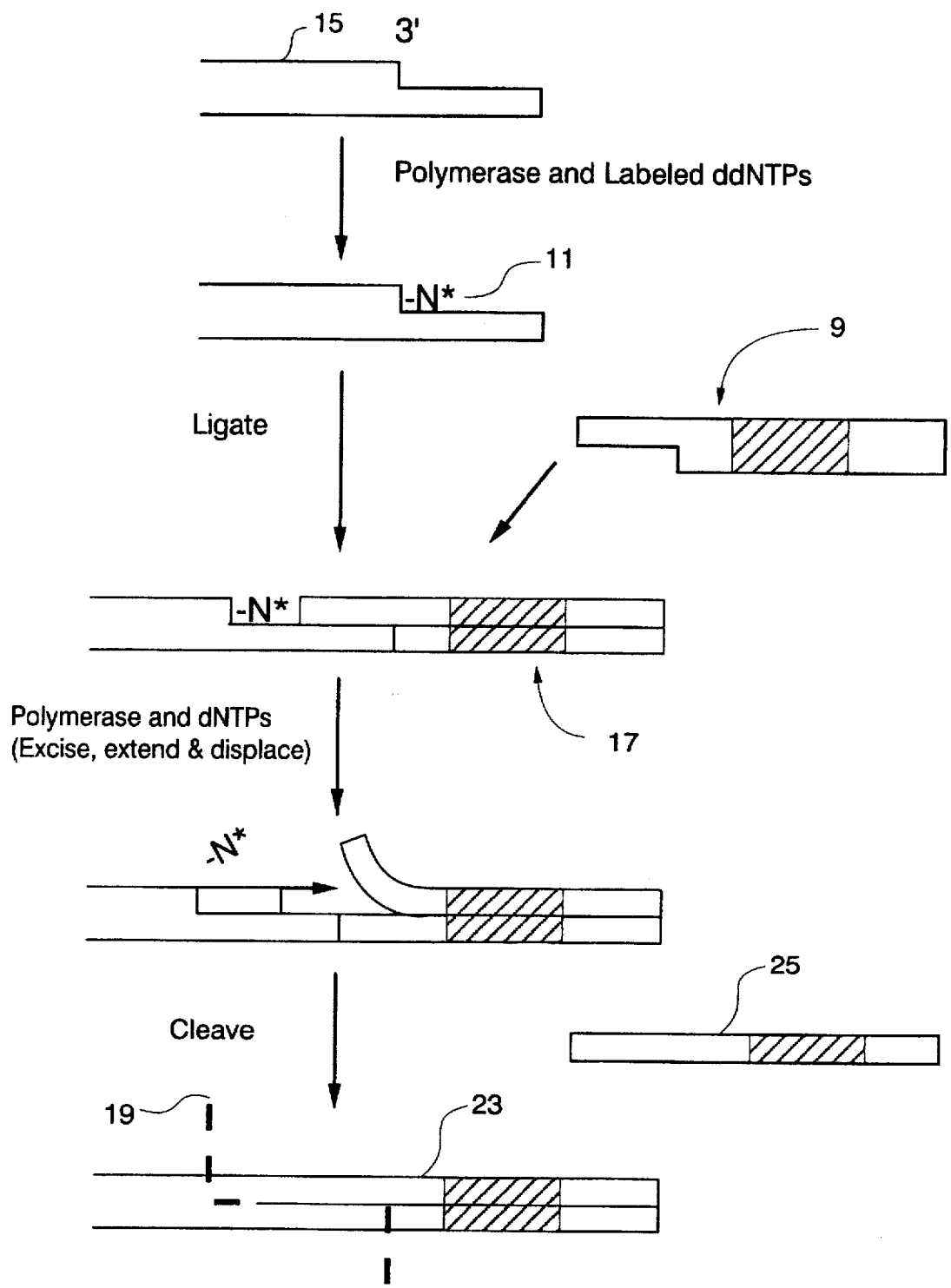
FIG. 1c illustrates steps of an embodiment wherein a nucleotide of the target polynucleotide is identified by extension with a polymerase in the presence of labeled dideoxynucleoside triphosphates followed by their excision, strand extension, and strand displacement.

An example of this embodiment is illustrated in FIG. 1b: The 3' recessed strand of polynucleotide (15) is extended with a nucleic acid polymerase in the presence of the four dideoxynucleoside triphosphates, each carrying a distinguishable fluorescent label, so that the 3' recessed strand is extended by one nucleotide (11), which permits its complementary nucleotide in the 5' protruding strand of polynucleotide (15) to be identified. Probe (9) having recognition site (12), spacer region (14), and complementary protruding strand (10), is then ligated to polynucleotide (15) to form ligated complex (17). Ligated complex (17) is then cleaved at cleavage site (19) to release a labeled fragment (21) and augmented probe (23). A shortened polynucleotide (15) with a regenerated 3' recessed strand is then ready for the next cycle of identification, ligation, and cleavage.

In such embodiments, the first nucleotide of the 5' protruding strand adjacent to the double stranded portion of the target polynucleotide is readily identified by extending the 3' strand with a nucleic acid polymerase in the presence of chain-terminating nucleoside triphosphates. Preferably, the 3' strand is extended by a nucleic acid polymerase in the presence of the four chain-terminating nucleoside triphosphates, each being labeled with a distinguishable fluorescent dye so that the added nucleotide is readily identified by the color of the attached dye. Such chain-terminating nucleoside triphosphates are available commercially, e.g. labeled dideoxynucleoside triphosphates, such as described by Hobbs, Jr. et al, U.S. Pat. No. 5,047,519; Cruickshank, U.S. Pat. No. 5,091,519; and the like. Procedures for such extension reactions are described in various publications, including Syvanen et al, Genomics, 8: 684–692 (1990); Goelet et al, International Application No. PCT/US92/01905; Livak and Brenner, U.S. Pat. No. 5,102,785; and the like.

A probe may be ligated to the target polynucleotide using conventional procedures, as described more fully below. Preferably, the probe is ligated after a single nucleotide extension of the 3' strand of the target polynucleotide. More preferably, the number of nucleotides in the protruding strand of the probe is the same as the number of nucleotides in the protruding strand of the target polynucleotide after the extension step. That is, if the nuclease provides a protruding strand having four nucleotides, then after the extension step the protruding strand will have three nucleotides and the protruding strand of the preferred probe will have three nucleotides.

The cleavage step in this embodiment may be accomplished by a variety of techniques, depending on the effect that the added chain-terminating nucleotide has on the efficiencies of the nuclease and/or ligase employed. Preferably, a ligated complex is formed with the presence of the labeled chain-terminating nucleotide, which is subsequently cleaved with the appropriate nuclease, e.g. a class IIs restriction endonuclease, such as Fok I, or the like.

In a preferred embodiment, after extension and ligation, the chain-terminating nucleotide may be excised. Preferably, this is carried out by the 3'→5' exonuclease activity (i.e. proof-reading activity) of a DNA polymerase, e.g. T4 DNA polymerase, acting in the presence of the appropriate nucleoside triphosphates. By the action of this enzyme, the chain-terminating nucleoside (11) is exchanged with a natural counterpart and the strand is extended, displacing the unligated probe strand (25). Conveniently, when probes having protruding stands are employed, this step simultaneously caps the target polynucleotides that failed to ligate to a probe in a preceding ligation step by "filling in" their ends thereby preventing subsequent ligation.

Such excision may also be carried out chemically, provided that the labeled chain-terminating nucleoside is attached by a labile bond, such as an acid-labile phosphoramidate bond. Synthesis of such nucleoside phosphoramidates and their use with DNA polymerases are described in Letsinger et al, J. Am. Chem. Soc., 94: 292–293 (1972) and Letsinger et al, Biochem., 15: 2810–2816 (1976). After identification, the phosphoramidate bond is cleaved and the nucleoside excised by mild acid to leave a terminal phosphate group which must be removed with a 3' phosphatase prior to the next cycle.

In another embodiment, the chain-terminating nucleotide is excised and the recessed 3' strand extended before ligation leaving a blunt-ended target polynucleotide. A subsequence cycle is then initiated by ligation of a blunt-ended probe to the end of the target polynucleotide. The use of a probe with a blunt end eliminates the need to employ multiple probes, because there are no protruding strands that have to be hybridized in order for ligation to take place.

In another variation of this embodiment, a nuclease is selected which leaves a one nucleotide 5' protruding strand after digestion, e.g. Alw I. Thus, chain extension need not be carried out in the presence of chain-terminating nucleoside triphosphates; ordinary deoxynucleoside triphosphates can be employed to leave a flush-ended polynucleotide. A blunt-ended probe is then used to initiate the next cycle. Preferably, the nucleoside triphosphates used are labeled, as would be the chain-terminating analogs described in the above embodiments. In further preference, the label is attached by way of a selectively cleavable bond, so that the label can be removed to enhance the efficiency of the nuclease in the subsequent cycle. Several such cleavable linkage moieties are available, e.g. Herman et al, Anal.

Biochem., 156: 48–55 (1986) (disulfide linker); Urdea U.S. Pat. Nos. 4,775,619 and 5,118,605.

Figure 1D:
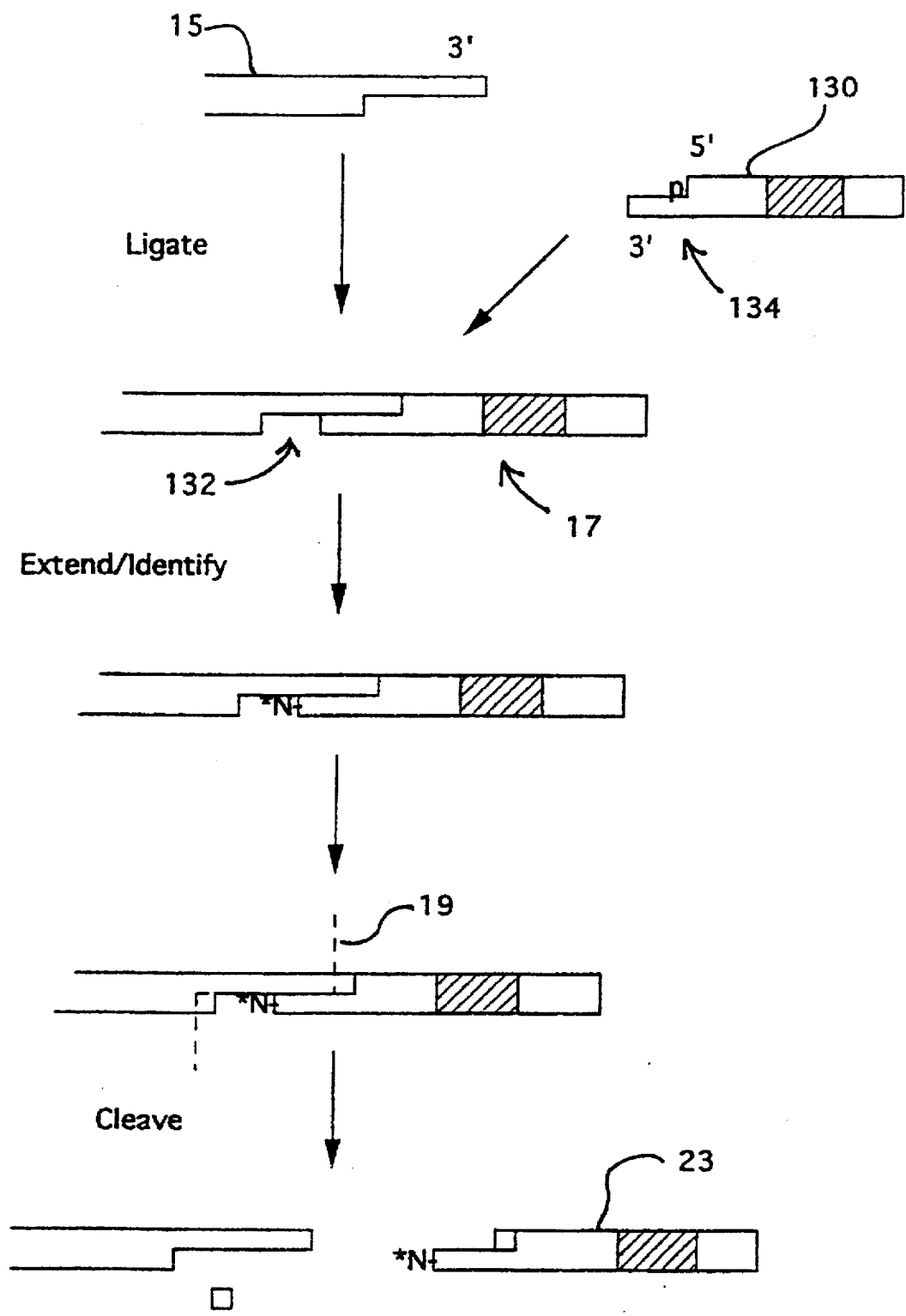
FIG. 1d diagrammatically illustrates an embodiment in which nucleotide identification is carried out by polymerase extension of a probe strand in the presence of labeled chain-terminating nucleoside triphosphates.

In yet another aspect of this embodiment, after ligation, a 3' end of a strand of the probe is extended with a DNA polymerase in the presence of labeled chain-terminating nucleoside triphosphates, as illustrated in FIG. 1d. There target polynucleotide (15) having a 3' protruding end is ligated to probe (130) having a complementary 3' protruding end (134) one nucleotide less in length. That is, when the 3' protruding strand (134) of probe (130) has three nucleotides, the 3' protruding strand of target polynucleotide (15) would have at least four nucleotides. Ligation results in the formation of ligated complex (17) with gap (132). Gap (132) is then filled by extending 3' protruding end (134) with a nucleic acid polymerase in the presence of chain-terminating nucleoside triphosphates. After cleavage, the cycle can be repeated.

Figure 1E:
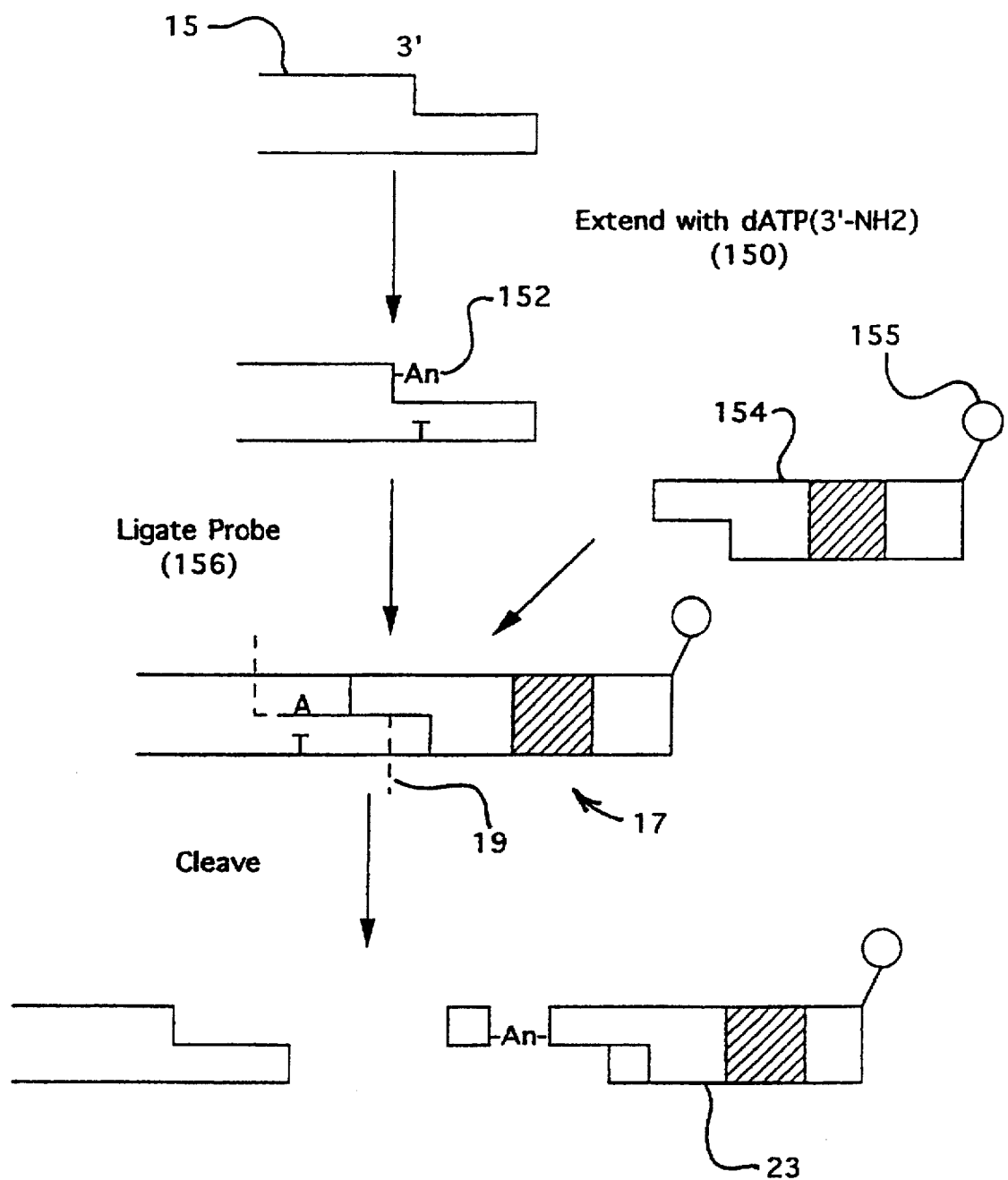
FIG. 1e diagrammatically illustrates an embodiment in which nucleotide identification is carried out by polymerase extension in the presence of unlabeled chain-terminating 3'-amino nucleoside triphosphates followed by ligation of a labeled probe.

This embodiment may also be implemented with unlabeled chain-terminating nucleoside triphosphates, as illustrated in FIG. 1e. Target polynucleotide (15) is successively exposed to different 3'-aminonucleoside triphosphates in the presence of a nucleic acid polymerase (150). The 3'-aminonucleoside triphosphates act as chain-terminators when incorporated. For example, 3'-aminoadenosine triphosphate (152) shown incorporated in FIG. 1e stops further strand extension and reduces the length of the protruding strand by one nucleotide, from 4 to 3. After such exposure, probe (154) with label (155) corresponding to the adenosine chain-terminator is mixed with the target sequence for ligation (156). As the labeled probe has a protruding strand of 3 nucleotides, it will only ligate if there has been an extension. If no ligation takes place, and no probe remains attached after washing, then the next 3'-aminonucleoside triphosphate and corresponding probe are tried. This process continues until the target polynucleotide is successfully extended and a corresponding probe is ligated to form ligated complex (17). The synthesis of 3'-aminonucleoside triphosphates are described in Kutateldze et al, FEBS Letters, 153: 420–426 (1983), Krayevsky et al, Biochimica et Biophysica Acta, 783: 216–220 (1984), and Herrlein et al, Helvetica Chimica Acta, 77: 586–598 (1994). The ligation properties of oligonucleotides having terminal 3'-aminonucleoside is described in Fung and Gryaznov, International application PCT/US94/03087. The chain terminating properties of 3'-aminonucleotides are described in Herrlein et al (cited above).

Figure 1F:
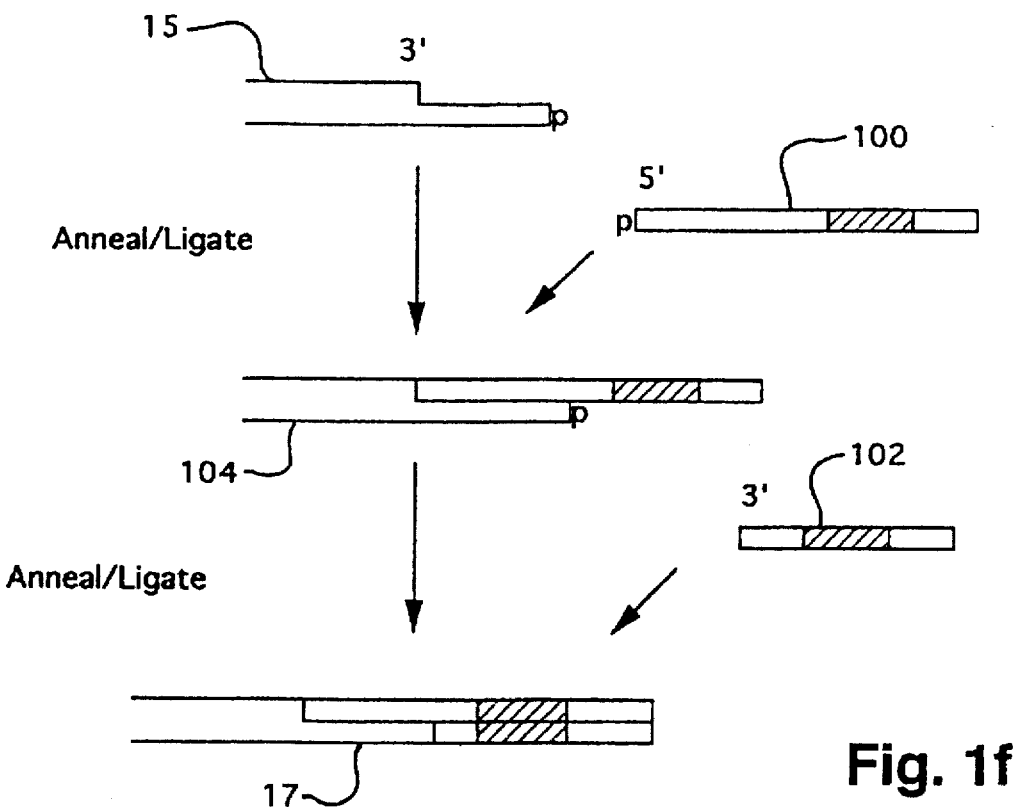
FIG. 1f illustrates probe assembly at the end of a target polynucleotide having a 5' protruding strand.

In yet another embodiment of the invention, a probe is assembled at the end of a target polynucleotide in two steps, as illustrated by the example in FIG. 1f. A first single stranded oligonucleotide (100) having a 5' monophosphate is annealed to and ligated with target polynucleotide (15) having a 5' monophosphate on its protruding strand to form a precursor (104) to ligated complex (17). A second single stranded oligonucleotide (102) complementary to the protruding strand of precursor (104) is annealed to and ligated with precursor (104) to form ligated complex (17). As with the double stranded probes described more fully below, first oligonucleotide (100) may be delivered to the target polynucleotide as a mixture and ligation preferably takes place at high stringency so that perfectly matched hybrids (between the protruding strand of the target polynucleotide and the 5' end of the first oligonucleotide) are preferentially ligated. Clearly, second oligonucleotide (102) need only have a sequence complementary to the protruding portion of precursor (104) so that a second ligation can take place to form ligated complex (17).

Figure 1G:
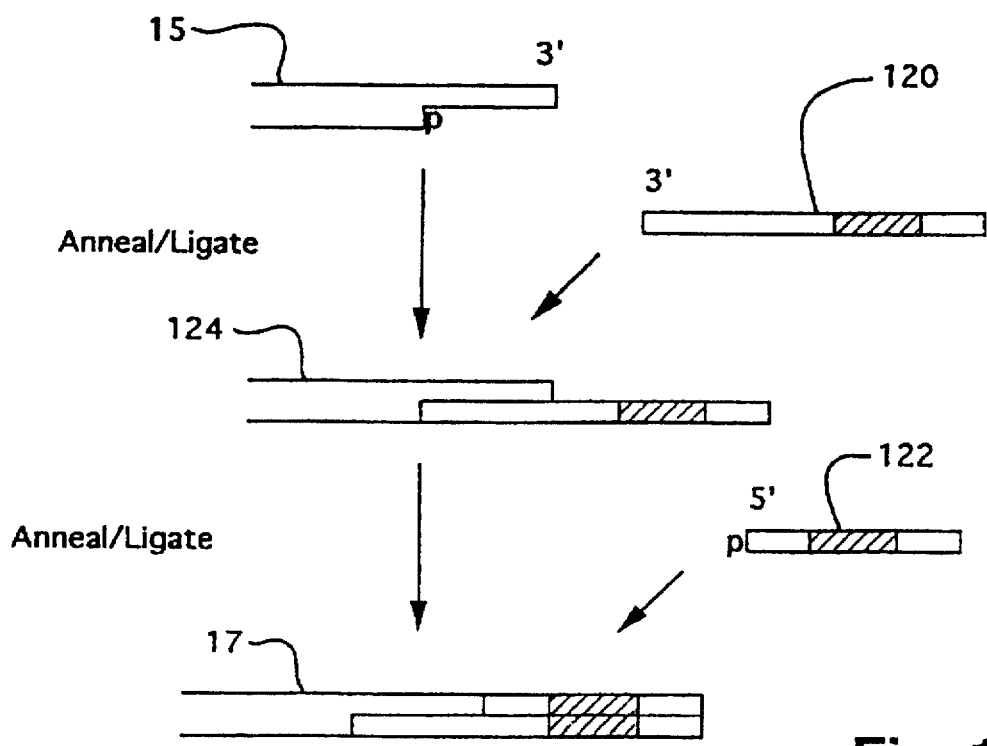
FIG. 1g illustrates probe assembly at the end of a target polynucleotide having a 3' protruding strand.

In another form of this embodiment, illustrated in FIG. 1g, a first single stranded oligonucleotide (120) is annealed to and ligated with target polynucleotide (15) having a 5' monophosphate on its recessed strand to form a precursor (124) to ligated complex (17). A second single stranded oligonucleotide (122) complementary to the protruding strand of precursor (124) and having a 5' monophosphate is annealed to and ligated with precursor (124) to form ligated complex (17). As with the double stranded probes described more fully below, first oligonucleotide (120) may be delivered to the target polynucleotide as a mixture and ligation preferably takes place at high stringency so that perfectly matched hybrids (between the protruding strand of the target polynucleotide and the 3' end of the first oligonucleotide) are preferentially ligated. As above, second oligonucleotide (122) need only have a sequence complementary to the protruding portion of precursor (124) so that a second ligation can take place to form ligated complex (17).

Synthesis of Probes

The complementary strands of the probes are conveniently synthesized on an automated DNA synthesizer, e.g. an Applied Biosystems, Inc. (Foster City, Calif.) model 392 or 394 DNA/RNA Synthesizer, using standard chemistries, such as phosphoramidite chemistry, e.g. disclosed in the following references: Beaucage and Iyer, Tetrahedron, 48: 2223–2311 (1992); Molko et al, U.S. Pat. No. 4,980,460; Koster et al, U.S. Pat. No. 4,725,677; Caruthers et al, U.S. Pat. Nos. 4,415,732; 4,458,066; and 4,973,679; and the like. Alternative chemistries, e.g. resulting in non-natural backbone groups, such as phosphorothioate, phosphoramidate, and the like, may also be employed provided that the resulting oligonucleotides are compatible with the ligation and cleavage reagents. After synthesis, the complementary strands are combined to form a double stranded probe. The protruding strand of a probe may be synthesized as a mixture, such that every possible sequence is represented in the protruding portion. For example, if the protruding portion consisted of four nucleotides, in one embodiment four mixtures are prepared as follows:

$X_1X_2 \ldots X_iNNNA$, $X_1X_2 \ldots X_iNNNC$, $X_1X_2 \ldots X_iNNNG$, and $X_1X_2 \ldots X_iNNNT$ where the "NNNs" represent every possible 3-mer and the "Xs" represent the duplex forming portion of the strand. Thus, each of the four probes listed above contains $4^3$ or 64 distinct sequences; or, in other words, each of the four probes has a complexity of 64. For example, $X_1X_2 \ldots X_iNNNA$ contains the following sequences:

| |
|---|
| $X_1X_2 \ldots X_iAAAA$ |
| $X_1X_2 \ldots X_iAACA$ |
| $X_1X_2 \ldots X_iAAGA$ |
| $X_1X_2 \ldots X_iAATA$ |
| $X_1X_2 \ldots X_iACAA$ |
| . |
| . |
| . |
| $X_1X_2 \ldots X_iTGTA$ |
| $X_1X_2 \ldots X_iTTAA$ |
| $X_1X_2 \ldots X_iTTCA$ |
| $X_1X_2 \ldots X_iTTGA$ |
| $X_1X_2 \ldots X_iTTTA$ |

Such mixtures are readily synthesized using well known techniques, e.g. as disclosed in Telenius et al, Genomics, 13:

718–725 (1992); Welsh et al, Nucleic Acids Research, 19: 5272–5279 (1991); Grothues et al, Nucleic Acids Research, 21: 1321–1322 (1993); Hartley, European patent application 90304496.4; and the like. Generally, these techniques simply call for the application of mixtures of the activated monomers to the growing oligonucleotide during the coupling steps where one desires to introduce multiple nucleotides. As discussed above, in some embodiments it may be desirable to reduce the complexity of the probes. This can be accomplished using complexity reducing analogs, such as deoxyinosine, 2-aminopurine, or the like, e.g. as taught in Kong Thoo Lin et al, Nucleic Acids Research, 20: 5149–5152, [or by] U.S. Pat. No. 5,002,867; Nichols et al, Nature, 369: 492–493 (1994); and the like.

Preferably, for oligonucleotides with phosphodiester linkages, the duplex forming region of a probe is between about 12 to about 30 basepairs in length; more preferably, its length is between about 15 to about 25 basepairs.

From the above, it is clear that the probes can have a wide variety of forms. For example, the probes can have the form $X_1X_2 \ldots X_iANNN$, $X_1X_2 \ldots X_iNANN$, $X_1X_2 \ldots X_iNNAN$, or the like. Or, the number of probe sets could be increased and the complexity reduced by constructing 16 sets of probes of 16-fold having the form: $X_1X_2 \ldots X_iNNAA$, $X_1X_2 \ldots X_iNNAC$, $X_1X_2 \ldots X_iNNAG$, and so on.

It is not crucial that the duplex forming region of each such set of probes have the same length. Size differences among the probes can be used as a means for identifying them, e.g. Skolnick et al, Genomics, 2: 273–279 (1988). Also, in some embodiments, it may be desirable to synthesize the probe as a single polynucleotide which contains self-complementary regions. After synthesis, the self-complementary regions are allowed to anneal to form a probe with a protruding strand at one end and a single stranded loop at the other end. Preferably, in such embodiments the loop region may comprise from about 3 to 10 nucleotides, or other comparable linking moieties, e.g. alkylether groups, such as disclosed in U.S. Pat. No. 4,914,210. Many techniques are available for attaching reactive groups to the bases or internucleoside linkages for labeling, as discussed below.

When conventional ligases are employed in the invention, as described more fully below, the 5' end of the probe may be phosphorylated in some embodiments. A 5' monophosphate can be attached to a second oligonucleotide either chemically or enzymatically with a kinase, e.g. Sambrook et al, Molecular Cloning: A Laboratory Manual, 2nd Edition (Cold Spring Harbor Laboratory, New York, 1989). Chemical phosphorylation is described by Horn and Urdea, Tetrahedron Lett., 27: 4705 (1986), and reagents for carrying out the disclosed protocols are commercially available, e.g. 5' Phosphate-ON™ from Clontech Laboratories (Palo Alto, Calif.). Thus, in some embodiments, probes may have the form:

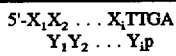

the form:

or the like, where the Y's are the complementary nucleotides of the X's and "p" is a monophosphate group.

Labeling Probes

The probes of the invention can be labeled in a variety of ways, including the direct or indirect attachment of radioactive moieties, fluorescent moieties, colorimetric moieties, and the like. Many comprehensive reviews of methodologies for labeling DNA and constructing DNA probes provide guidance applicable to constructing probes of the present invention. Such reviews include Matthews et al, Anal. Biochem., Vol 169, pgs. 1–25 (1988); Haugland, Handbook of Fluorescent Probes and Research Chemicals (Molecular Probes, Inc., Eugene, 1992); Keller and Manak, DNA Probes, 2nd Edition (Stockton Press, New York, 1993); and Eckstein, editor, Oligonucleotides and Analogues: A Practical Approach (IRL Press, Oxford, 1991); Wetmur, Critical Reviews in Biochemistry and Molecular Biology, 26: 227–259 (1991); and the like. Many more particular methodologies applicable to the invention are disclosed in the following sample of references: Connolly, Nucleic Acids Research, Vol. 15, pgs. 3131–3139 (1987); Gibson et al, Nucleic Acids Research, Vol. 15, pgs. 6455–6467 (1987); Spoat et al, Nucleic Acids Research, Vol. 15, pgs. 4837–4848 (1987); Fung et al, U.S. Pat. No. 4,757,141; Hobbs, Jr., et al U.S. Pat. No. 5,151,507; Cruickshank, U.S. Pat. No. 5,091,519; (synthesis of functionalized oligonucleotides for attachment of reporter groups); Jablonski et al, Nucleic Acids Research, 14: 6115–6128 (1986)(enzyme-oligonucleotide conjugates); and Urdea et al, U.S. Pat. No. 5, 124,246 (branched DNA). Attachment sites of labeling moieties are not critical in embodiments relying on probe labels to identify nucleotides in the target polynucleotide, provide that such labels do not interfere with the ligation and cleavage steps. In particular, dyes may be conveniently attached to the end of the probe distal to the target polynucleotide on either the 3' or 5' termini of strands making up the probe, e.g. Eckstein (cited above), Fung (cited above), and the like. In some embodiments, attaching labeling moieties to interior bases or inter-nucleoside linkages may be preferred.

Preferably, the probes are labeled with one or more fluorescent dyes, e.g. as disclosed by Menchen et al, U.S. Pat. No. 5,188,934; Begot et al PCT application PCT/US90/05565. More preferably, pairs of dyes using fluorescence energy transfer are employed on each probe as taught by Ju et al, Proc. Natl. Acad. Sci., 92: 4347–4351 (1995) and Ju et al, Nature Medicine, 2: 246–249 (1996).

Figure 1H:
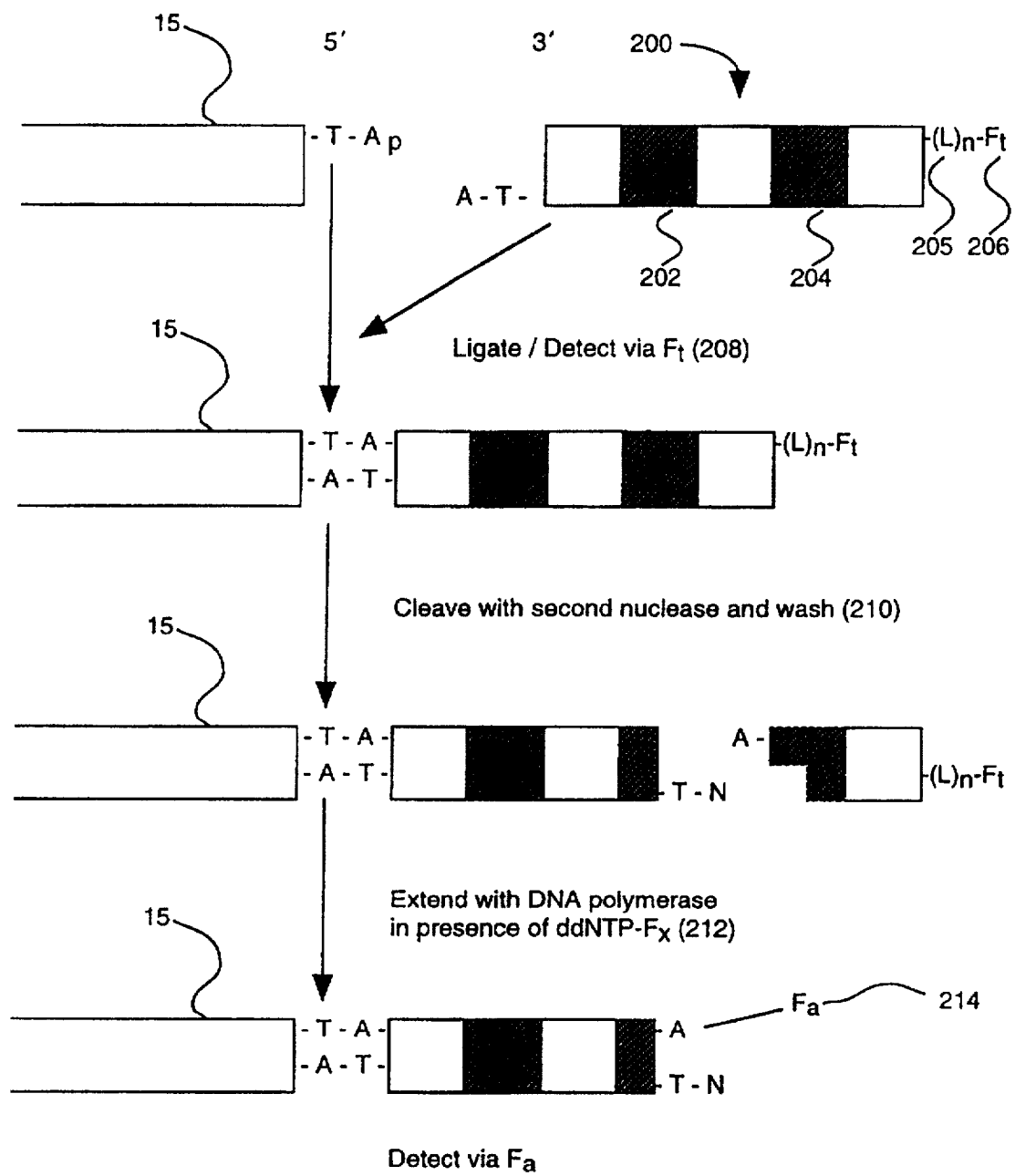
FIG. 1h illustrates an embodiment employing a probe for identifying two nucleotides of a target polynucleotide in each cycle of ligation and cleavage.

Multiple labels on a single probe may be used to identify multiple nucleotides during a single cycle of ligation. An exemplary probe that permits identification of two nucleotides per ligation cycle is shown in FIG. 1h. Probe (200) has a two base overhang with a sequence "AT." Sixteen such probes are provided, each with a different two-nucleotide sequence in the overhang. Generally, a first reporter group (206) is employed to generate a signal that identifies one of the nucleotides after a successful ligation. The subscript "t" indicates a thymidine occupies the penultimate position at the 5' end of the lower strand of target polynucleotide (15). After a signal from the first reporter group, $F_r$, is measured, then the reporter is removed or inactivated either to reveal a second reporter group or to permit a second reporter group to be attached.

Preferably, the first reporter group is cleaved from the probe. Such cleavage may be accomplished enzymatically or chemically, e.g. by introducing a chemically scissile internucleosidic linkage, such as a N3'→P5'-phosphoramidate between the reporter and the rest of the probe, which could be cleaved by mild acid treatment. Chemically scissile internucleosidic linkages may be cleaved by treating them with characteristic chemical or physical conditions, such as an oxidizing environment, a reducing environment, light of a characteristic wavelength (for photolabile linkages), or the like. Other examples of chemically scissile internucleosidic linkages which may be used in accordance with the invention are described in Urdea 5,380,833; Gryaznov et al, Nucleic Acids Research, 21: 1403-1408 (1993) (disulfide); Gryaznov et al, Nucleic Acids Research, 22: 2366-2369 (1994) (bromoacetyl); Urdea et al, International application PCT/US91/05287 (photolabile); and like references.

Further chemically scissile linkages that may be employed with the invention include chain-terminating nucleotides that may be chemically converted into an extendable nucleoside. Examples of such compounds are described in the following references: Canard et al, Internation application PCT/FR94/00345; Ansorge, German patent application No. DE 4141178 A1; Metzker et al, Nucleic Acids Research, 22: 4259-4267 (1994); Cheeseman, U.S. Pat. 5,302,509; Ross et al, International application PCT/US90/06178; and the like. In these embodiments, the first reporter group is attached to a first chain-terminating nucleoside triphosphate which is incorporated after ligation. The nucleoside incorporated corresponds to one of the nucleotides at the ligation site. As taught in Cheeseman (cited above), the first reporter group is removed from the incorporated nucleoside rendering the strand in which it is located capable of being extended by a polymerase. Further nucleotides are identified at the ligation site by further rounds of incorporation and reporter group cleavage.

A first reporter group may also be removed enzymatically, as exemplified in FIG. 1h. Probe (200) has type IIs nuclease recognition site (202) and second nuclease recognition site (204) which releases first reporter group F, (206) and optional linker arm "—(L)ₙ—" (205) upon digestion with its corresponding restriction endonuclease. After ligation and detection (208) of the signal generated by the first reporter group, the ligated complex is cleaved (210) by the second nuclease and washed to leave a protruding 5' strand that can serve as a template for extending the 3' strand of the probe at the cleavage site. The first nucleotide in the 5' protruding strand (i.e. the one closest to the double stranded portion) is known so that when the 3' strand is extended (212) by a DNA polymerase in the presence of four labeled didexoynucleoside triphosphates the incorporated dideoxynucleotide gives the identify of the nucleotide of the 5' strand which, in turn, gives the identity of the second nucleotide at the ligation site, as is indicated by the subscript "a" of second reporter group $F_a$ (214). Several restriction endonucleases are available that have recognition sites that permit the selection of any nucleotide for the first nucleotide of the 5' protruding strand. For example, the second nuclease may be selected from the following group: Fnu 4H I (GC/NGC), Scr FI (CC/NGG), Ear I (CTCTTC(¼)), Bsa I (GGTCTC (⅕), and the like.

Linker arm (205) may be employed to minimize the interaction between the first reporter group and the double stranded portion of the probe. Preferably, the linker arm comprises a linear oligomer of inert and non-sterically hindering subunits, L, connected by phosphorus (V) linkages. L may simply comprise a single stranded "tail" of nucleosides, or L may comprise other non-nucleosidic moieties, such as alkyl, alkenyl, and/or ethers containing 2-3 carbon atoms, e.g. as described in Jaschke et al, Tetrahedron Letters, 34: 301-304 (1992); Ma et al, International application PCT/CA92/00423; Zon et al, International application PCT/US90/06630; Durand et al, Nucleic Acids Research, 18: 6353-6359 (1990); Salunkhe et al, J. Am. Chem. Soc., 114: 8768-8772 (1992); and the like.

The first reporter may also be cleave enzymatically by RNase H treatment. In this embodiment, a probe is constructed as follows, which is shown below as having a two-nucleotide ("AT") protruding strand:

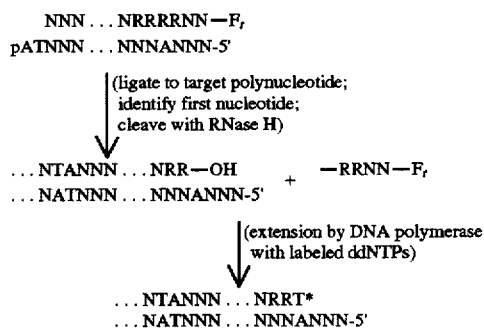

where "RRRR" represents a sequence of four ribonucleotides in the probe, and $F_r$ is a first reporter group, as described above, and T* is a second reporter group, e.g. an incorporated dideoxynucleotide. Such mixed RNA-DNA oligonucleotides are readily synthesized using conventional automated DNA synthesizers, e.g. Duck et al, U.S. Pat. No. 5,011,769. RNase H will cleave the probe specifically in the center of the four ribonucleotide segment, Hogrefe et al, J. Biol. Chem., 265: 5561-5566 (1990), leaving a 3' hydroxyl on the upper strand. Thus, the ribonucleotides of the upper strand may be extended with a DNA polymerase in the presence of labeled dideoxynucleoside triphosphates.

In some embodiments, it may be desirable to use one or two signal generating moieties, such as one or two types of fluorescent dye, in a sequencing operation. Under such conditions, a sequence can be characterized by the presence or absence of a particular nucleotide at consecutive locations along a polynucleotide. For example, the sequence, "acggttaat" can be described in terms of the presence and absence of t's, expressed as: "(not t)-(not t)-(not t)o(not t)-tt-(not t)-(not t)-t". Or, such a sequence may be described in terms of the presence and absence of purines, expressed as: "purine-(not purine)-purine-purine-(not purine)-(not purine) -purine-purine-(not purine)". Preferably, two dyes are employed in such embodiments so that a positive signal is measured, even to show the absence of a particular nucleotide or base. Such binary sequences may be used to uniquely identify polynucleotides from a population, such as a cDNA library, provided the sequence is long enough.

A single signal generating moiety, such as a single fluorescent dye, may be employed when sequencing several different target polynucleotides attached to different spatially addressable solid phase supports, in a parallel sequencing operation such as described in International patent application PCT/US95/12791. This may be accomplished by providing four sets of probes that would be applied sequentially to the plurality of target polynucleotides. Exemplary set of such probes are shown below:

| Set 1 | Set 2 | Set 3 | Set 4 |
|---|---|---|---|
| ANNNN...NN | dANNNN...NN | dANNNN...NN | dANNNN...NN |
| N...NNTT...T* | d N...NNTT...T | N...NNTT...T | N...NNTT...T |
| dCNNNN...NN | CNNNN...NN | dCNNNN...NN | dCNNNN...NN |
| N...NNTT...T | N...NNTT...T* | N...NNTT...T | N...NNTT...T |
| dGNNNN...NN | dGNNNN...NN | GNNNN...NN | dGNNNN...NN |
| N...NNTT...T | N...NNTT...T | N...NNTT...T* | N...NNTT...T |
| dTNNNN...NN | dTNNNN...NN | dTNNNN...NN | TNNNN...NN |
| N...NNTT...T | N...NNTT...T | N...NNTT...T | N...NNTT...T* | where each of the listed probes represents a mixture of $4^3$=64 oligonucleotides such that the identity of the 3' terminal nucleotide of the top strand is fixed and the other positions in the protruding strand are filled by every permutation of a sequence of three nucleotides, or complexity reducing analogs. The listed probes are also shown with a single stranded poly-T tail with a signal generating moiety attached to the terminal thymidine, shown as "T*". The "d" on the unlabeled probes designates a ligation-blocking moiety or absense of 3'-hydroxyl, which prevents unlabeled probes from being ligated. Preferably, such 3'-terminal nucleotides are dideoxynucleotides. In this embodiment, the probes of set 1 are first applied to a plurality of target polynucleotides and treated with a ligase so that target polynucleotides having a thymidine complementary to the 3' terminal adenosine of the labeled probes are ligated. The unlabeled probes are simultaneously applied to minimize inappropriate ligations. The locations of the target polynucleotides that form ligated complexes with probes terminating in "A" are identified by the signal generated by the label carried on the probe. After washing and cleavage, the probes of set 2 are applied. In this case, target polynucleotides forming ligated complexes with probes terminating in "C" are identified by location. Similarly, the probes of sets 3 and 4 are applied and locations of positive signals identified. The process of sequentially applying the four sets of probes continues until the desired number of nucleotides are identified on the target polynucleotides.

In another embodiment, two labels, e.g. fluorescent dyes, may be employed to alternatively identify purines and pyrimidines in a parallel DNA sequencing scheme such as described in International patent application PCT/US95/12791. Two sets of probes are provided having recognition sites for different type IIs nucleases, i.e. a first nuclease and a second nuclease. The nucleases are selected to leave identical kinds of overhangs after cleavage. Probes of each set are labeled either with a first label or a second label depending on whether they are designed to produce a successful ligation in the presence of A or G, respectively, for the first set, or in the presence of C or T, respectively, for the second set. The probes of both sets are applied to a collection of immobilized target polynucleotides with an appropriate protruding strand and ligated in accordance with the invention. The positions and characteristics, e.g. colors, of the signals generated by the labels are recorded. Next, the ligated probes are cleaved with the first nuclease and washed. The sites where the signals disappear correspond to sites where A's and G's were present in the target polynucleotide and the sites where the signals remain correspond to sites with C's and T's present in the target polynucleotide. The probes are then cleaved with the second nuclease to complete the cycle of ligation and nuclease cleavage.

Ligation of Probes

In accordance with the invention, a probe of the invention is ligated to an end of a target polynucleotide to form a ligated complex in each cycle of ligation and cleavage. The ligated complex is the double stranded structure formed after probe and target are ligated, usually after the protruding strands of the target polynucleotide and probe anneal and at least one pair of the identically oriented strands are caused to be covalently linked to one another. Ligation can be accomplished either enzymatically or chemically. Chemical ligation methods are well known in the art, e.g. Ferris et al, Nucleosides & Nucleotides, 8: 407–414 (1989); Shabarova et al, Nucleic Acids Research, 19: 4247–4251 (1991); and the like. Preferably, however, ligation is carried out enzymatically using a ligase in a standard protocol. Many ligases are known and are suitable for use in the invention, e.g. Lehman, Science, 186: 790–797 (1974); Engler et al, DNA Ligases, pages 3–30 in Boyer, editor, The Enzymes, Vol. 15B (Academic Press, New York, 1982); and the like. Preferred ligases include T4 DNA ligase, T7 DNA ligase, E. coli DNA ligase, Taq ligase, Pfu ligase, and Tth ligase. Protocols for their use are well known, e.g. Sambrook et al (cited above); Barany, PCR Methods and Applications, 1: 5–16 (1991); Marsh et al, Strategies, 5: 73–76 (1992); and the like. Generally, ligases require that a 5' phosphate group be present for ligation to the 3' hydroxyl of an abutting strand. This is conveniently provided for at least one strand of the target polynucleotide by selecting a nuclease which leaves a 5' phosphate, e.g. as Fok I.

In a preferred embodiment of the invention employing unphosphorylated probes, the step of ligating includes (i) ligating the probe to the target polynucleotide with a ligase so that a ligated complex is formed having a nick on one strand, (ii) phosphorylating the 5' hydroxyl at the nick with a kinase using conventional protocols, e.g. Sambrook et al (cited above), and (iii) ligating again to covalently join the strands at the nick, i.e. to remove the nick.

Preparation of Target Polynucleotides

Preferably, a target polynucleotide for use in the invention is double stranded and is prepared so that it has a protruding strand at least one end. The protruding strand may be either 5' or 3' and, preferably, the number of nucleotides in the protruding portion of the strand is in the range of from 2 to 6. A target polynucleotide is referred to as "−k" where k is some integer, e.g. usually between 2 and 6, whenever the 5' strand is protruding. Conversely, a target polynucleotide is referred to as "+k" whenever the 3' strand is protruding. For example the following would be a −4 target polynucleotide in accordance with this nomenclature:

5'-AACGTTAC...
  AAATG...

In one preferred embodiment of the invention, the target polynucleotide is anchored to a solid phase support, such as a magnetic particle, polymeric microsphere, filter material, or the like, which permits the sequential application of reagents without complicated and time-consuming purification steps. The length of the target polynucleotide can vary widely; however, for convenience of preparation, lengths employed in conventional sequencing are preferred. For example, lengths in the range of a few hundred basepairs, 200–300, to 1 to 2 kilobase pairs are preferred.

The target polynucleotides can be prepared by various conventional methods. For example, target polynucleotides can be prepared as inserts of any of the conventional cloning vectors, including those used in conventional DNA sequencing. Extensive guidance for selecting and using appropriate cloning vectors is found in Sambrook et al, Molecular Cloning: A Laboratory Manual, Second Edition (Cold Spring Harbor Laboratory, New York, 1989), and like references. Sambrook et al and Innis et al, editors, PCR Protocols (Academic Press, New York, 1990) also provide guidance for using polymerase chain reactions to prepare target polynucleotides. Preferably, cloned or PCR-amplified target polynucleotides are prepared which permit attachment to magnetic beads, or other solid supports, for ease of separating the target polynucleotide from other reagents used in the method. Protocols for such preparative techniques are described fully in Wahlberg et al, Electrophoresis, 13: 547–551 (1992); Tong et al, Anal. Chem., 64: 2672–2677 (1992); Hultman et al, Nucleic Acids Research, 17: 4937–4946 (1989); Hultman et al, Biotechniques, 10: 84–93 (1991); Syvanen et al, Nucleic Acids Research, 16: 11327–11338 (1988); Dattagupta et al, U.S. Pat. No. 4,734, 363; Uhlen, PCT application PCT/GB89/00304; and like references. Kits are also commercially available for practicing such methods, e.g. Dynabeads™ template preparation kit from Dynal AS. (Oslo, Norway).

Populations of target polynucleotides may be prepared in parallel by the use of microparticles, e.g. magnetic beads, controlled pore glass particles, or the like, that each have a uniform population of adaptors attached. The adaptor is an oligonucleotide between about 30 and 100 nucleotides in length that comprises regions for PCR primer binding, regions that form restriction endonuclease cleavage sites when duplexes are established, and an address region of about 12–15 nucleotides that permits capture of a unique target polynucleotide by hybridization. Such adaptors may also comprise other linking moieties known in the art, e.g. polyethylene glycol arms, or the like. The population of adaptors on a particular microparticle is uniform in the sense that each oligonucleotide has the same sequence, so that the same target polynucleotide would be captured by different adaptors on the same microparticle. Preparation of microparticle with uniform populations of oligonucleotides is disclosed in PCT publications WO 92/00091, WO 92/03461, and like references. For parallel sequencing, target polynucleotides are prepared in a library whose vector contains complementary address regions adjacent to the target polynucleotide insert. After excision and denaturing, the population of target polynucleotide-which now each have a complementary address region on its terminus-are mixed with a population of microparticles under conditions that permit capture. Individual particles with captured target polynucleotides may be isolated and manipulated on a microscope slide, e.g. as taught by Lam et al, PCT publication WO 92/00091 and Lam et al, Science, 354: 82–84 (1991).

Cleavage of Ligated Probes

"Nuclease" as the term is used in accordance with the invention means any enzyme, combination of enzymes, or other chemical reagents, or combinations chemical reagents and enzymes that when applied to a ligated complex, discussed more fully below, cleaves the ligated complex to produce an augmented probe and a shortened target polynucleotide. A nuclease of the invention need not be a single protein, or consist solely of a combination of proteins. A key feature of the nuclease, or of the combination of reagents employed as a nuclease, is that its (their) cleavage site be separate from its (their) recognition site. The distance between the recognition site of a nuclease and its cleavage site will be referred to herein as its "reach." By convention, "reach" is defined by two integers which give the number of nucleotides between the recognition site and the hydrolyzed phosphodiester bonds of each strand. For example, the recognition and cleavage properties of Fok I is typically represented as "GGATG(9/13)" because it recognizes and cuts a double stranded DNA as follows:

| | |
|---|---|
| 5'-... NNGGATGNNNNNNNNN | NNNNNNNNNN ... |
| 3'-... NNCCTACNNNNNNNNNNNNN | NNNNNN ... | where the bolded nucleotides are Fok I's recognition site and the N's are arbitrary nucleotides and their complements.

It is important that the nuclease only cleave the target polynucleotide after it forms a complex with its recognition site; and preferably, the nuclease leaves a protruding strand on the target polynucleotide after cleavage.

Cleavage with a nuclease can be accomplished using chemical nucleases, e.g. as disclosed by Sigman et al, Arm. Rev. Biochem., 59: 207–236 (1990); Le Doan et al, Nucleic Acid Research, 15: 7749–7760 (1987); U.S. Pat. No. 4,795, 700; Francois et al, Proc. Natl. Acad. Sci., 86: 9702–9706 (1989); and like references. Preferably, such embodiments comprise an oligonucleotide moiety linked to a cleavage moiety, wherein the oligonucleotide moiety recognizes the ligated complex by triple helix formation. There is extensive guidance in the literature for selecting appropriate sequences, orientation, conditions, nucleoside type (e.g. whether ribose or deoxyribose nucleosides are employed), base modifications (e.g. methylated cytosine, and the like) in order to maximize, or otherwise regulate, triplex stability as desired in particular embodiments, e.g. Roberts et al, Proc. Natl. Acad. Sci., 88: 9397–9401 (1991); Roberts et al, Science, 258: 1463–1466 (1992); Distefano et al, Proc. Natl. Acad. Sci., 90: 1179–1183 (1993); Mergny et al, Biochemistry, 30: 9791–9798 (1991); Cheng et al, J. Am. Chem. Soc., 114: 4465–4474 (1992); Beal and Dervan, Nucleic Acids Research, 20: 2773–2776 (1992); Beal and Dervan, J. Am. Chem. Soc., 114: 4976–4982 (1992); Giovannangeli et al, Proc. Natl. Acad. Sci., 89: 8631–8635 (1992); Moser and Dervan, Science, 238: 645–650 (1987); McShan et al, J. Biol. Chem., 267: 5712–5721 (1992); Yoon et al, Proc. Natl. Acad. Sci., 89: 3840–3844 (1992); Blume et al, Nucleic Acids Research, 20: 1777–1784 (1992); and the like. Preferably, such chemical nucleases are employed with an exonuclease which can produce a protruding strand after cleavage. Although current chemical nucleases are limited in that their cleavage sites vary around an expected site, they can be employed in fingerprinting, sequence comparisons, and other uses that only require partial sequence information.

Preferably, nucleases employed in the invention are natural protein endonucleases (i) whose recognition site is separate from its cleavage site and (ii) whose cleavage results in a protruding strand on the target polynucleotide. Most preferably, class IIs restriction endonucleases are employed as nucleases in the invention, e.g. as described in Szybalski et al. Gene, 100: 13–26 (1991); Roberts et al, Nucleic Acids Research, 21: 3125–3137 (1993); and Livak and Brenner, U.S. Pat. No. 5,093,245. Exemplary class IIs nucleases for use with the invention include Alw XI, Bsm AI, Bbv I, Bsm FI, Sts I, Hga I, Bsc AI, Bbv II, Bee fl, Bce 85I, Bcc I, Bcg I, Bsa I, Bsg I, Bsp MI, Bst 71 I, Ear I, Eco 57I, Esp 3I, Fau I, Fok I, Gsu I, Hph I, Mbo II, Mme I, Rle AI, Sap I, Sfa NI, Taq II, Tth 111II, Bco 5I, Bpu AI, Fin I, Bsr DI, and isoschizomers thereof. Preferred nucleases include Fok I, Hga I, Ear I, and Sfa NI.

Preferably, prior to nuclease cleavage steps, usually at the start of a sequencing operation, the target polynucleotide is treated to block the recognition sites and/or cleavage sites of the nuclease being employed. This prevents undesired cleavage of the target polynucleotide because of the fortuitous occurrence of nuclease recognition sites at interior locations in the target polynucleotide. Blocking can be achieved in a variety of ways, including methylation and treatment by sequence-specific aptamers, DNA binding proteins, or oligonucleotides that form triplexes. Whenever natural protein endonucleases are employed, recognition sites can be conveniently blocked by methylating the target polynucleotide with the cognate methylase of the nuclease being used. That is, for most if not all type II bacterial restriction endonucleases, there exists a so-called "cognate" methylases that methylates its recognition site. Many such methylases are disclosed in Roberts et al (cited above) and Nelson et al, Nucleic Acids Research, 21: 3139–3154 (1993), and are commercially available from a variety of sources, particularly New England Biolabs (Beverly, Mass.). Alternatively, if a PCR step is employed in preparing target polynucleotides for sequencing, 5-methylcytosine triphosphates may be used during amplification so that the natural cytosine are replaced by methylated cytosines in the amplicon. This later approach has the added advantage of eliminating the need to treat a target polynucleotide bound to a solid phase support with another enzyme.

Figure 2:
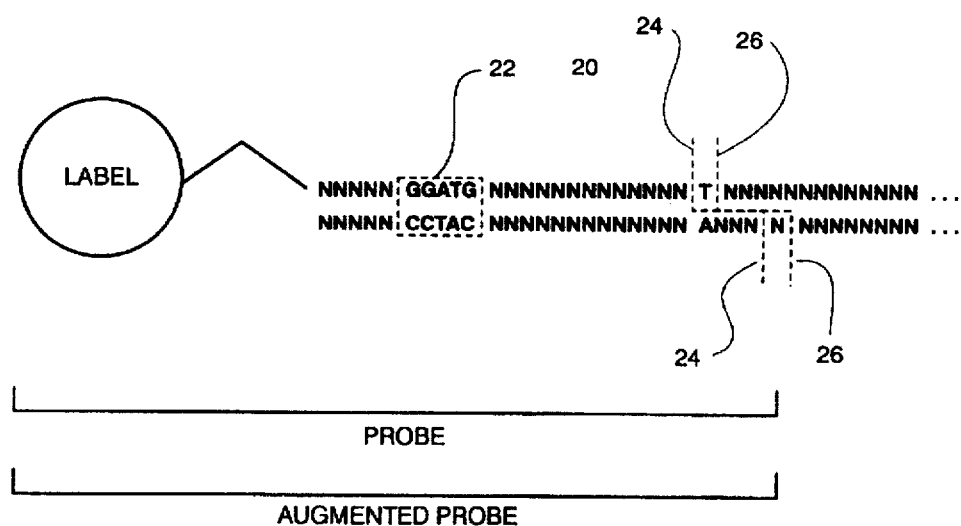
FIG. 2 illustrates the relative positions of the nuclease recognition site, ligation site, and cleavage site in a ligated complex.

In accordance with the invention, after a probe is ligated to the target polynucleotide to form a ligated complex, the ligated complex is cleaved with a nuclease to give an augmented probe and a shortened target polynucleotide. This occurs because the probe is designed such that the distance from the recognition site of the probe to end of the probe is less than the distance from the recognition site to the cleavage site of the nuclease. That is, the nuclease necessarily cleaves in a region of the target polynucleotide, thereby shortening it by one or more nucleotides in each cycle, as illustrated in FIG. 2. Conversely, in each cycle the probe has one or more nucleotides added to it after cleavage to form an augmented probe. In FIG. 2, ligated complex 20 is shown with recognition site 22 of the Fok I nuclease. The terminus 24 of the probe is one nucleotide to the left of the Fok I cleavage site 26. Thus, in the illustrated embodiment, ligation leads to the identification of the terminal thymidine on the target polynucleotide and cleavage results in the shortening of each strand of the target polynucleotide by one nucleotide. The nucleotides removed by the cleavage together with the probe to which they remain attached form an augmented probe.

As mentioned above, the method of the invention is preferably carried out in the following steps: (a) ligating a probe to an end of the polynucleotide having a protruding strand to form a ligated complex, the probe having a complementary protruding strand to that of the polynucleotide and the probe having a nuclease recognition site; (b) removing unligated probe from the ligated complex; (c) identifying one or more nucleotides in the protruding strand of the polynucleotide; (d) cleaving the ligated complex with a nuclease; and (e) repeating steps (a) through (d) until the nucleotide sequence of the polynucleotide is determined. Identification of the one or more nucleotides in the protruding strand of the target polynucleotide is carried out either before or after the cleavage step, depending on the embodiment of the invention being implemented. Identification of the one or more nucleotides in the protruding strand of the target polynucleotide is carried out either before or after the cleavage step, depending on the embodiment of the invention being implemented. Detection prior to cleavage is preferred in embodiments where sequencing is carried out in parallel on a plurality of sequences (either segments of a single target polynucleotide or a plurality of altogether different target polynucleotides), e.g. attached to separate magnetic beads, or other types of solid phase supports. Detection either before or after cleavage may be carried out in embodiments where a homogeneous population of target polynucleotides is being analyzed, e.g. a population of solid phase supports, such as magnetic beads, all have the identical target polynucleotide attached. In such cases, other factors my dictate the ordering of the detection and cleavage steps, such as the detection scheme being employed, whether the sequencing reactions are being carried out in separate reaction mixtures or whether they take place in a common mixture, and the like.

Capping Steps

In further preference, the method of the invention includes one or more capping steps in each cycle. The term "capping" is used herein by analogy with the usage of the term in polynucleotide synthesis, e.g. Andrus et al, U.S. Pat. No. 4,816,571. It refers to a treatment of target polynucleotides that have failed to undergo, or participate in, a transformation of a prior step. The capping treatment is designed to render a target polynucleotide inert to participation in any treatment steps of subsequent cycles. In this manner spurious signals from "out of phase" cleavages or ligations are prevented. Capping steps may be implemented after ligation steps and/or cleavage steps. For example, a first capping step may be implemented after unligated probe is washed from the target polynucleotide. If the nuclease being employed leaves a 5' protruding strand on the target polynucleotides, capping is preferably accomplished by exposing the unreacted target polynucleotides to a mixture of the four dideoxynucleoside triphosphates, or other chain-terminating nucleoside triphosphates, and a DNA polymerase. The DNA polymerase extends the 3' strand of the unreacted target polynucleotide by one chain-terminating nucleotide, e.g. a dideoxynucleotide, thereby rendering it incapable of ligating in subsequent cycles.

A second capping step may be implemented after the cleavage step. Depending on the recognition site of the type IIs nuclease employed, probes that fail to cleave may be "capped" by treatment with a methylase to block the type IIs recognition site in the probe, thereby rendering the ligated complex inert to further processing steps. Probes may also be constructed that include an additional restriction site that permits capping by cleavage of probes that fail to cleave under treatment by the type IIs nuclease. An example of such a probe is shown below: SEQ. ID. No. 41)

```
5'-... NNGGATGNGATATCN
3'-... NNCCTACNCTATAGNNNNN
```
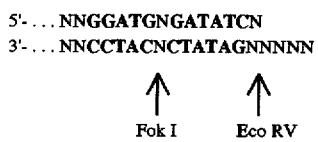

Treatment with Eco RV results in the formation of a blunt ended target polynucleotide that will be incapable of participating in subsequent ligations (in embodiments requiring protruding ends). Such capping approaches have the added advantage of removing any labels that may be attached to the terminus of the ligated probe, thereby reducing a contribution to noise in subsequent detection steps.

Clearly, one of ordinary skill in the art could combine features of the embodiments set forth above to design still further embodiments in accordance with the invention, but not expressly set forth above.

Use of Multiple Cleavage Enzymes

An important aspect of the invention is "multiple stepping," or the simultaneous use of a plurality of nucleases which cleave at different distances from the ligation site to sequence a target polynucleotide. The use of multiple nucleases having different reaches permits one to periodically "restart" the sequencing process by capping sequences involved in prior or current cycles of ligation and cleavage and by beginning a new cycle of ligation and cleavage on a "fresh" set of target polynucleotides whose protruding strands are exposed by cleavage with a long reach nuclease. By employing multiple nucleases in this manner the number of nucleotides that can be determined on a set of target polynucleotides can be increased over that which can be done with a single nuclease.

In using multiple nucleases it is important that one be able to convert the protruding stand of a target polynucleotide from one form to another. For example, one may wish to apply both Fok I (which leaves a –4 target polynucleotide) and Ear I (which leave a –3 target polynucleotide) to a target sequence, i.e. "double stepping". As described more fully below, in order to do this, one must be able to convert the –4 target polynucleotide to a –3 target polynucleotide without loss of information. This can be accomplished by providing a conversion probe that has the following properties: i) a protruding strand compatible with the current target polynucleotide protruding strand, i.e. having the same number of nucleotides in antiparallel orientation, ii) a nuclease recognition site of the nuclease being converted to, and iii) a spacer region selected so that the cut site of the new nuclease corresponds to at least one of the ligation sites of the two strands. Preferably, the conversion probe permits ligation of only one strand and one of the unligated sites, i.e. nicks, is located at the cleavage site of the nuclease being converted to.

Figure 3A:
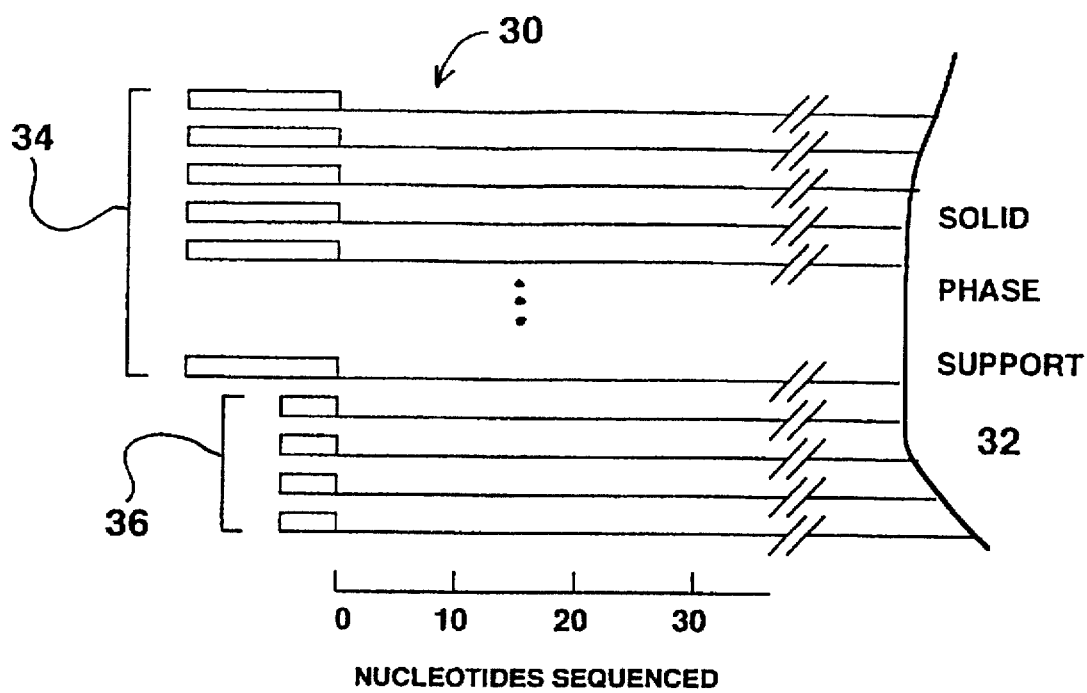
FIGS. 3a through 3h diagrammatically illustrate the embodiment referred to herein as "double stepping," or the simultaneous use of two different nucleases in accordance with the invention.
Figure 3B:
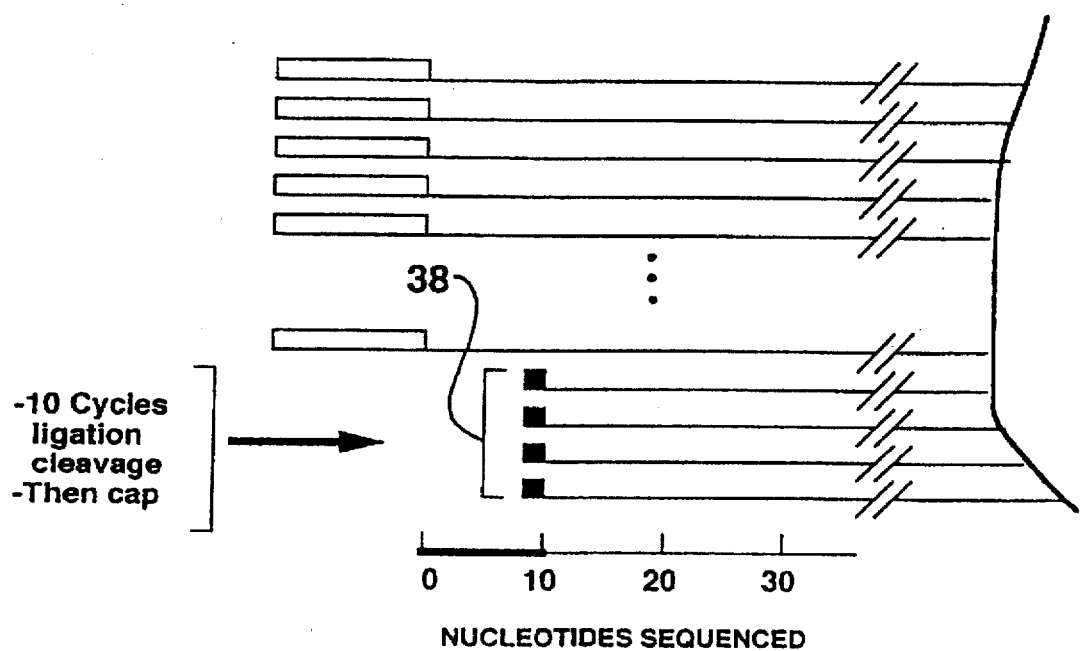
Figure 3C:
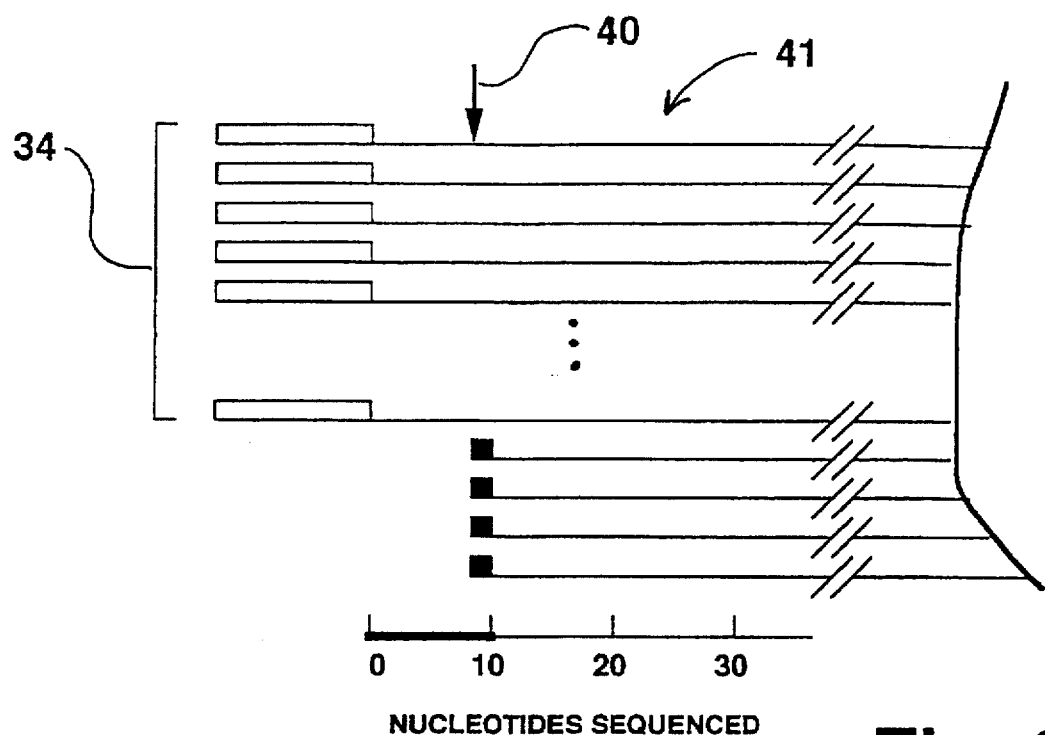
Figure 3D:
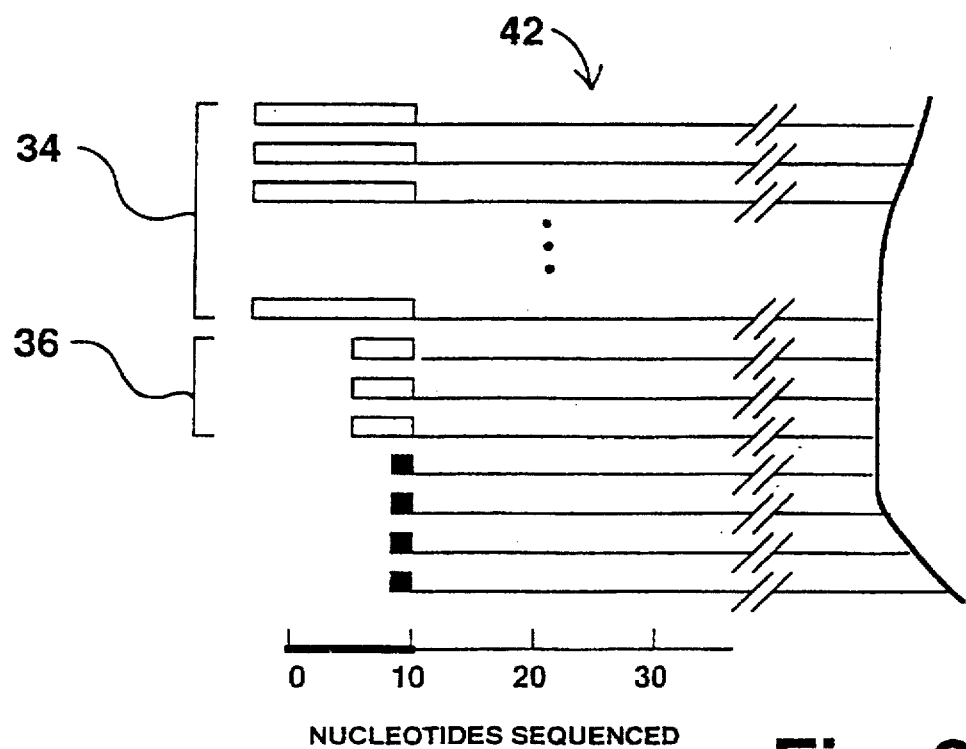
Figure 3E:
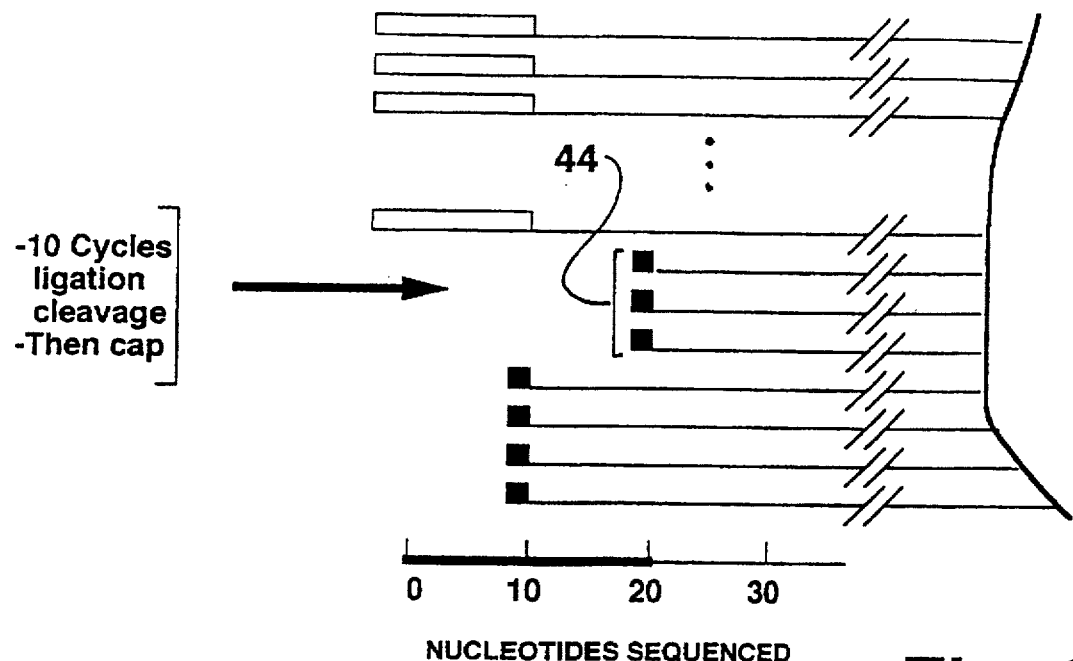
Figure 3F:
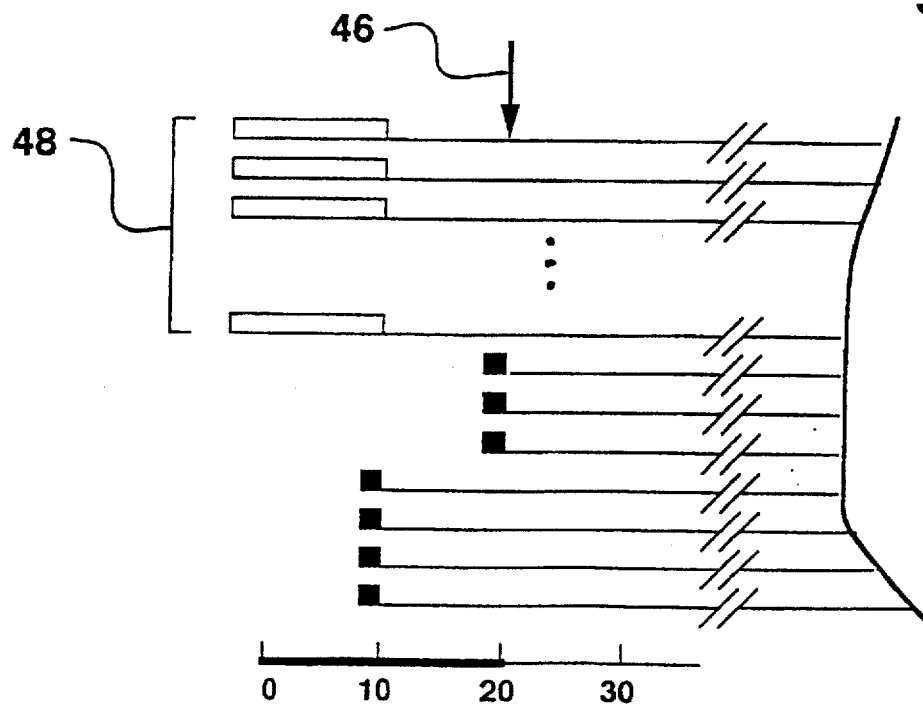

FIGS. 3a through 3h diagrammatically illustrate this aspect of the invention in the case where two nucleases are employed, a first nuclease which permits cleavage ten nucleotides from the ligation site and a second nuclease which permits cleavage of one nucleotide from the ligation site. The process illustrated in figure is readily generalized to more than two nucleases. In FIG. 3a, a mixture of probes 34 and 36 are ligated to the target polynucleotides 30 attached to solid phase support 32. Probe 34 contains a nuclease recognition site of a first nuclease that has a long reach, e.g. ten nucleotides, and a short spacer region so that its associated nuclease cleaves deeply into the target polynucleotide. Probe 36 converts (if necessary) the protruding strand of the target polynucleotides (initially prepared for the first nuclease) to a protruding strand corresponding to a second nuclease used to cleave the target polynucleotide one nucleotide at a time. With the appropriate protruding strand available, the second nuclease is employed in nine cycles of ligation and cleavage followed by a capping step to give the identity of the first nine nucleotides of the target polynucleotide. As illustrated in FIG. 3b, capped sequences 38 no longer participate in ligation and cleavage cycles. The number of capped sequences produced in this step depends on the mixture of the two probes employed which, in turn, depends on several factors, including the length of the target polynucleotide, the nature of the label on the probes, the efficiencies of ligation and cleavage of the enzymes employed, and the like. The target polynucleotides 41 are then cleaved at 40 with the first nuclease, shown in FIG. 3c, to produce appropriate protruding strands at the termini of the target polynucleotides and the identity of the tenth nucleotide. After cleavage and washing, a mixture of probes 34 and 36 are ligated to the non-capped target polynucleotides 42 (FIG. 3d) to form ligated complexes. The ligated complexes including probe 36 are cleaved to convert the protruding strands of their associated target polynucleotides to protruding strands corresponding to the second nuclease, after which another nine cycles of ligation and cleavage take place followed by a capping step, to form a second set of capped sequences 44 (FIG. 3e). In this series of cycles the identities of nucleotides 11 through 19 are determined.

Figure 3G:
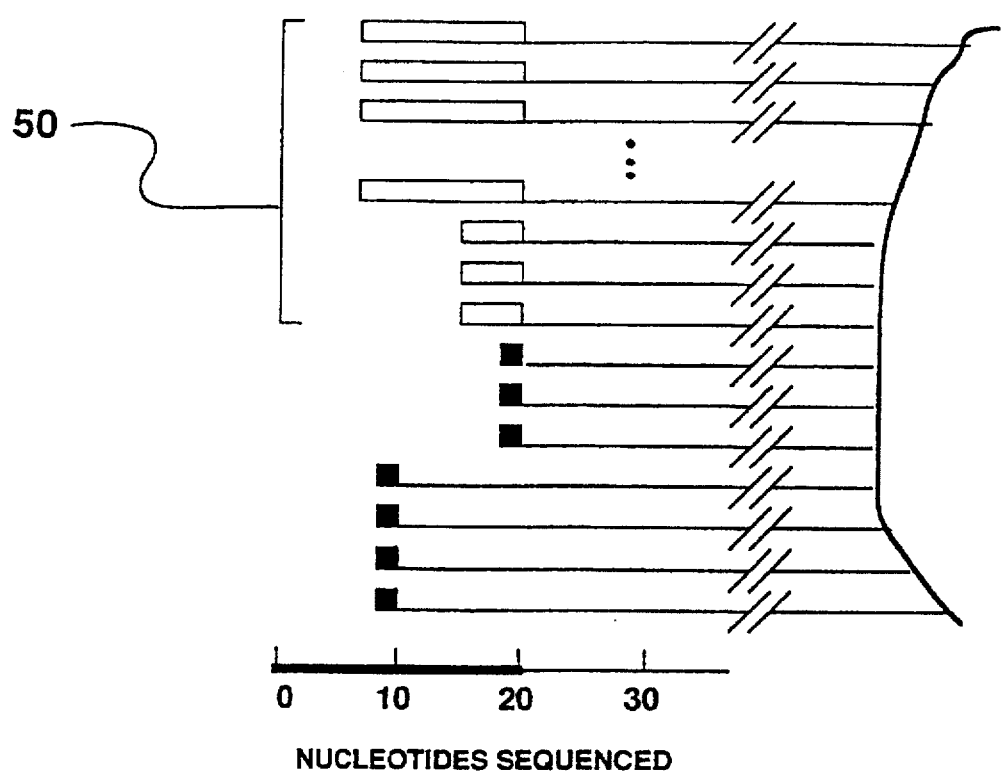
Figure 3H:
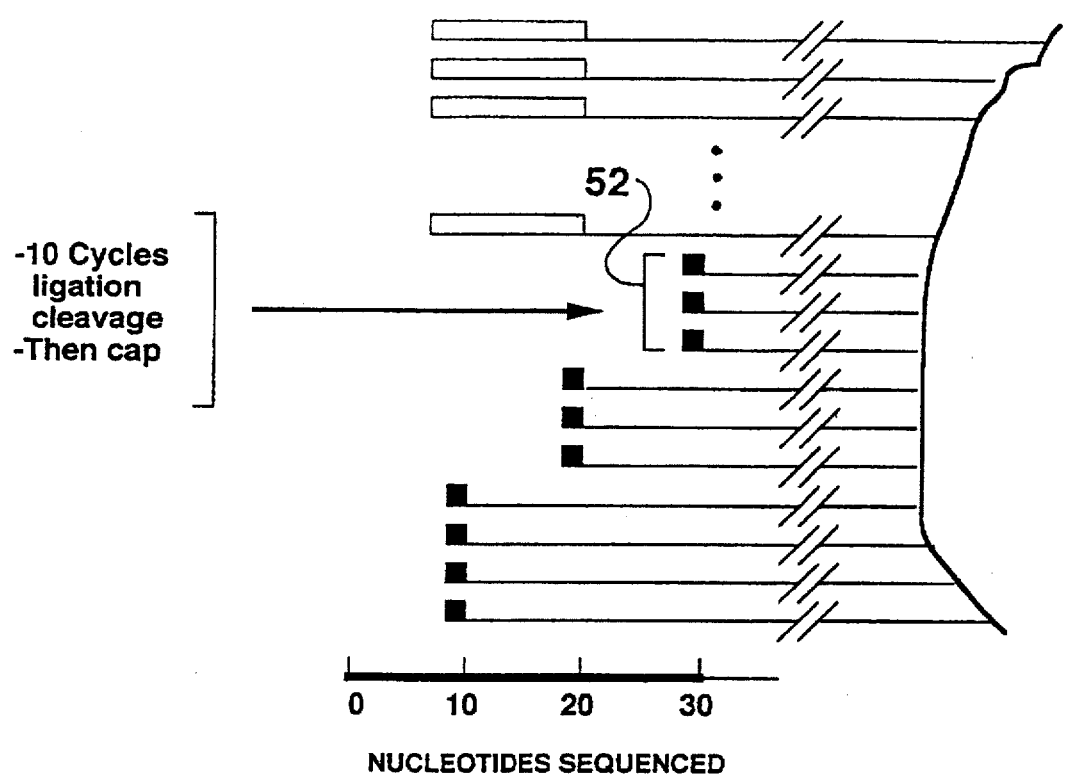

Next the target polynucleotides are cleaved with the first nuclease at 46 (in FIG. 3f) to produce protruding strands on target polynucleotides 48, after which a mixture of probes 34 and 36 are ligated to the target polynucleotides to form ligated complexes 50 (FIG. 3g). The ligated complexes comprising probe 36 are again cleaved to convert the protruding strands of their associated target polynucleotides to ones corresponding to the second nuclease, after which nine cycles of ligation and cleavage take place followed by a capping step, to form a third set of capped sequences 52 (FIG. 3h). This set of cycles leads to the identification of nucleotides 21 through 29.

This process continues until the nucleotide sequence of the target polynucleotide is determined or until the remaining population of target polynucleotides is too small to generate a detectable signal.

The invention includes systems and apparatus for carrying out sequencing automatically. Such systems and apparatus can take a variety of forms depending on several design constraints, including i) the nature of the solid phase support used to anchor the target polynucleotide, ii) the degree of parallel operation desired, iii) the detection scheme employed; iv) whether reagents are re-used or discarded, and the like. Generally, the apparatus comprises a series of reagent reservoirs, one or more reaction vessels containing target polynucleotide, preferably attached to a solid phase support, e.g. magnetic beads, one or more detection stations, and a computer controlled means for transferring in a predetermined manner reagents from the reagent reservoirs to and from the reaction vessels and the detection stations. The computer controlled means for transferring reagents and controlling temperature can be implemented by a variety of general purpose laboratory robots, such as that disclosed by Harrison et al, Biotechniques, 14: 88–97 (1993); Fujita et al, Biotechniques, 9: 584–591 (1990); Wada et al, Rev. Sci. Instrum., 54: 1569–1572 (1983); or the like. Such laboratory robots are also available commercially, e.g. Applied Biosystems model 800 Catalyst (Foster City, Calif.).

A variety of kits are provide for carrying out different embodiments of the invention. Generally, kits of the invention include probes tailored for the nuclease and the detection scheme of the particular embodiment. Kits further include the nuclease reagents, the ligation reagents, and instructions for practicing the particular embodiment of the invention. In embodiments employing natural protein endonucleases and ligases, ligase buffers and nuclease buffers may be included. In some cases, these buffers may be identical. Such kits may also include a methylase and its reaction buffer and a kinase and its reaction buffer. Preferably, kits also include a solid phase support, e.g. magnetic beads, for anchoring target polynucleotides. In one preferred kit, fluorescently labeled probes are provided such that probes corresponding to different terminal nucleotides of the target polynucleotide carry distinct spectrally resolvable fluorescent dyes. As used herein, "spectrally resolvable" means that the dyes may be distinguished on basis of their spectral characteristics, particularly fluorescence emission wavelength, under conditions of operation. Thus, the identity of the one or more terminal nucleotides would be correlated to a distinct color, or perhaps ratio of intensities at different wavelengths. More preferably, four such probes are provided that allow a one-to-one correspondence between each of four spectrally resolvable fluorescent dyes and the four possible terminal nucleotides on a target polynucleotide. Sets of spectrally resolvable dyes are disclosed in U.S. Pat. Nos. 4,855,225 and 5,188,934; International application PCT/US90/05565; and Lee et al, Nucleic Acids Research, 20: 2471–2483 (1992).

EXAMPLE 1

Sequencing a Target Polynucleotide Amplified from pUC19

A 368 basepair fragment of pUC19 is amplified by PCR for use as a test target polynucleotide. The 5' terminal nucleotide of the coding strand is at position 393 and the 3' terminal nucleotide of the coding strand is at position 740, Yanisch-Perron et al, Gene, 33: 103–119 (1985), so that the polylinker region is spanned. Two primers 18-mer primers employed having sequences 5'-AGTGAATTCGAGCTCGGT (SEQ ID NO: 1) and 5'-xCCTTTGAGTGAGCTGATA (SEQ ID NO: 2), where "x" is an amino linking group, Aminolinker II (Applied Biosystems, Inc., Foster City, Calif.), to which a biotin moiety is attached using manufacturer's protocol, 5' Biotin NIO-Label Kit (Clontech Laboratories, Palo Alto, Calif.). The amplified target polynucleotide is isolated and attached to streptavidin-coated magnetic beads (Dynabeads) using manufacturer's protocol, Dynabeads Template Preparation Kit, with M280-streptavidin (Dynal, Inc., Great Neck, N.Y.). A sufficient quantity of the biotinylated 393 basepair fragment is provided to load about 300 μg of Dynabeads M280-Streptavidin. After loading onto the Dynabeads, the target polynucleotides are digested with Eco RI and washed to provide a 5'-monophosphorylated protruding strand with an overhang of four nucleotides, i.e. a −4 target polynucleotide, shown below (SEQ ID NO: 3 and SEQ ID NO:4).

```
5'-pAATCGAGCTCGGTACCCGGGGATCCTCTA . . .
       GCTCGAGCCATGGGCCCCTAGGAGAT . . .
```

Reactions and washes below are generally carried out in 50 μL volumes of manufacturer's (New England Biolabs') recommended buffers for the enzymes employed, unless otherwise indicated. Standard buffers are also described in Sambrook et al, Molecular Cloning, 2nd Edition (Cold Spring Harbor Laboratory Press, 1989). Note that in this test example, methylation is not required because no Fok I recognition sequences are present in the target polynucleotide.

The following four sets of mixed probes (SEQ ID NO: 5 and SEQ ID NO: 6, SEQ ID NO: 5 and SEQ ID NO: 7, SEQ ID NO: 5 and SEQ ID NO: 8, SEQ ID NO: 5 and SEQ ID NO: 9, respectively) are provided for addition to the target polynucleotide:

```
TAMRA- ATCGGATGACATCAAC
       TAGCCTACTGTAGTTGANNN
FAM-   ATCGGATGACATCAAC
       TAGCCTACTGTAGTTGCNNN
ROX-   ATCGGATGACATCAAC
       TAGCCTACTGTAGTTGGNNN
JOE-   ATCGGATGACATCAAC
       TAGCCTACTGTAGTTGTNNN
``` where TAMRA, FAM, ROX, and JOE are spectrally resolvable fluorescent labels attached by way of Aminolinker II (all being available from Applied Biosystems, Inc., Foster City, Calif.); the bold faced nucleotides are the recognition site for Fok I endonuclease, and "N" represents any one of the four nucleotides, A, C, G, T. TAMRA (tetramethylrhodamine), FAM (fluorescein), ROX (rhodamine X), and JOE (2',7'-dimethoxy-4',5'-dichlorofluorescein) and their attachment to oligonucleotides is also described in Fung et al, U.S. Pat. No. 4,855,225.

Each of the above probes is separately incubated in sequence in approximately 5 molar excess of the target polynucleotide ends as follows: the probe is incubated for 60 minutes at 16° C. with 200 units of T4 DNA ligase and the anchored target polynucleotide in 50 μL of T4 DNA ligase buffer; after washing, the target polynucleotide is then incubated with 100 units T4 polynucleotide kinase in the manufacturer's recommended buffer for 30 minutes at 37° C., washed, and again incubated for 30 minutes at 16° C. with 200 units of T4 DNA ligase and the anchored target polynucleotide in 50 μL of T4 DNA ligase buffer. Washing is accomplished by immobilizing the magnetic bead support with a magnet and successively adding then removing 50 μL volumes of wash buffer, e.g. TE, disclosed in Sambrook et al (cited above). After the cycle of ligation-phosphorylation-ligation and a final washing, the beads are interrogated for the presence of fluorescent label. On the fourth set of such incubations, the characteristic fluorescence of JOE is detected indicating that the terminal nucleotide is A. The labeled target polynucleotide, i.e. the ligated complex, is then incubated with 10 units of Fok I in 50 μL of manufacturer's recommended buffer for 30 minutes at 37° C., followed by washing in TE. As a result the target polynucleotide is shortened by one nucleotide on each strand and is ready for the next cycle of ligation and cleavage. The process is continued until the desired number of nucleotides are identified.

EXAMPLE 2

Converting a −4 Protruding Strand to a −3 Protruding Strand

A −4 protruding strand is converted into a −3 protruding strand using the conversion probe shown below having an Ear I recognition site (indicated in bold) and a protruding strand whose terminal nucleotide is non-phosphorylated (indicated in lower case). The conversion probe is (SEQ ID NO: 10) ligated to the terminus of the target polynucleotide (SEQ ID NO: 11) using conditions as described in Example 1:

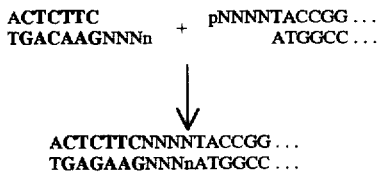

After ligation, the complex (SEQ ID NO: 12) is digested with Ear I using manufacturer's recommended protocol to give a target polynucleotide with a −3 protruding strand:

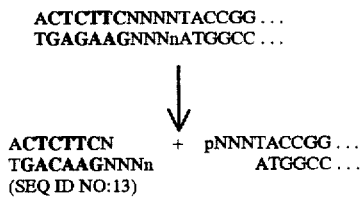

EXAMPLE 3

Convening a −4 Protruding Strand to a −5 Protruding Strand

A −4 protruding strand is convened into a −5 protruding strand using the conversion probe shown below having an Hga I recognition site (indicated in bold) and a protruding strand whose terminal nucleotide is non-phosphorylated (indicated in lower case). The conversion probe (SEQ ID NO: 14 and SEQ ID NO: 15) is ligated to the terminus of the target polynucleotide (SEQ ID NO: 16) using conditions as described in Example 1:

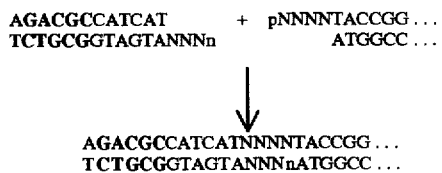

After ligation, the complex (SEQ ID NO: 17) is digested with Hga I using manufacturer's recommended protocol to give a target polynucleotide (SEQ ID NO: 18) with a −5 protruding strand:

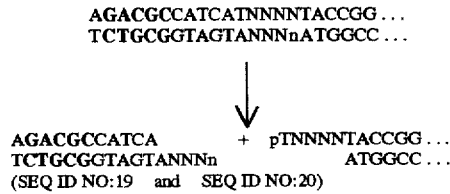

EXAMPLE 4

Convening a +2 Protruding Strand to a −5 Protruding Strand

A +2 protruding strand is convened into a −3 protruding strand using the conversion probe shown below having an Ear I recognition site (indicated in bold) and a protruding strand whose terminal nucleotide is non-phosphorylated (indicated in lower case). The conversion probe (SEQ ID NO: 21) is ligated to the terminus of the target polynucleotide using conditions as described in Example 1:

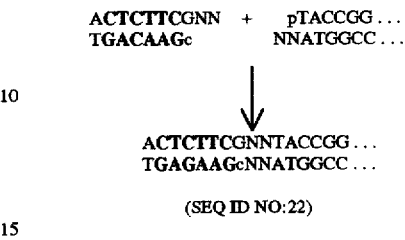

(SEQ ID NO:22)

After ligation, the complex (SEQ ID NO: 22) is digested with Ear I using manufacturer's recommended protocol to give a target polynucleotide with a −3 protruding strand:

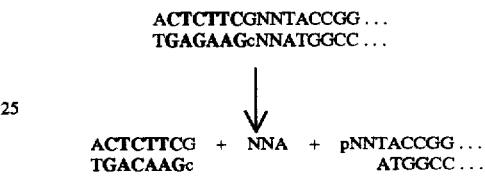

EXAMPLE 5

Double Stepping: Sequencing by Ligation Employing Two Restriction Endonucleases Two nucleases, Ear I and Fok I, with different reaches are used in the same sequencing operation. The procedure is illustrated in FIG. 3. A 368 basepair fragment of pUC19 with a −4 protruding strand is prepared as described in Example 1. Because the fragment contains a Ear I site (but no Fok I site), the target polynucleotide is initially treated with an Ear I methylase, e.g. as described in Nelson et al, Nucleic Acids Research, 17: r398–r415 (1989). Afterwards, a 9:1 mixture of the following two probes, Probe A: Probe B, is combined in about 5 molar excess with the target polynucleotide, ligated, kinased, and ligated, as described in Example 1 to form two populations of ligated complexes: about 10% terminating with Probe B (SEQ ID NO: 24 and SEQ ID NO: 25) and about 90% terminating with Probe A (SEQ ID NO: 23).

| Probe (A): | ATCGGATG<br>TAGCCTACNNNn | (Fok I recognition site) |
|---|---|---|
| Probe (B): | CAGATCCTCTTCa<br>GTCTAGGACAAGTNNNN | (Ear I recognition site) |

The target polynucleotide are then digested with Ear I to convert about 10% of the ligated complexes to a target polynucleotide having a −3 protruding strand. The following probes are then used in nine cycles of ligation-phosphorylation-ligation/identification/cleavage as described in Example 1 to give the identity of the first nine nucleotides.

| Ear I Probes |
|---|
| (SEQ ID NO: 26 and SEQ ID NO: 27, SEQ ID NO: 26 and SEQ ID NO: 28, SEQ ID NO: 26 and SEQ ID NO: 29, SEQ ID NO: 26 and SEQ ID NO: 30, respectively) |
| TAMRA- CAGATCCTCTTC GTCTAGGAGAAGGNN |
| FAM- CAGATCCTCTTC GTCTAGGAGAAGCNN |
| ROX- CAGATCCTCTTC GTCTAGGAGAAGANN |
| JOE- CAGATCCTCTTC GTCTAGGAGAAGTNN |

After the ninth cleavage and washing, the subpopulation of target polynucleotides that underwent the nine cycles of cleavage are capped by treating with a DNA polymerase in the presence of the four dideoxynucleoside triphosphates. After washing again, the target polynucleotides are digested with Fok I to give target polynucleotides with a –4 protruding strand. Thus, at this point 10% of the original population of target polynucleotides is 9 nucleotides shorter (on average) and capped and 90% are precisely 9 nucleotides shorter and ready for successive cycles of cleavage and ligation.

To the Fok I digested target polynucleotides is added an 8:1 mixture of Probe A: Probe B in a ligase buffer as described above. This results in approximately the same quantity of target polynucleotide being prepared for Ear I digestion as above. Alternatively, a constant ratio of Probe A: Probe B could be employed throughout the sequencing operation, which would lead to a less intense signal at each successive Fok I digestion step, but may also permit a longer sequence to be determined. Ear I is added to the resulting mixed population of ligated complexes under the manufacturer's recommended protocol to convert a subpopulation to target polynucleotides with –3 protruding strands. The Ear I probes are again applied nine times as described above to provide the identity of nucleotides 10 through 18. The process is continued as described above until the identities of the 90 terminal nucleotides of the target polynucleotide are obtained.

EXAMPLE 6

Sequencing a Target Polynucleotide Amplified from pGEM7Z: Identification of Nucleotides by the Ligation Reaction In this example, a segment of plasmid pGEM7Z (Promega, Madison, Wis.) was amplified and attached to glass beads via a double stranded DNA linker, one strand of which was synthesized directly onto (and therefore covalently linked to) the beads. In each sequencing cycle after ligation, an aliquot of beads was removed from the reaction mixture and loaded onto a gel electrophoresis column for analyzing the non-covalently bound strand of the ligated complex. The probes were designed so that the non-covalently bound strand would always carry a fluorescent label for analysis.

A 47-mer oligonucleotide was synthesized directly on KF169 Ballotini beads using a standard automated DNA synthesizer protocol. The complementary strand to the 47-mer was synthesized separately and purified by HPLC. When hybridized the resulting duplex has a Bst XI restriction site at the end distal from the bead. The complementary strand was hybridized to the attached 47-mer in the following mixture: 25 µl complementary strand at 200 pmol/µl; 20 mg KF169 Ballotini beads with the 47-mer; 6 µl New England Biolabs #3 restriction buffer; and 25 distilled water. The mixture was heated to 93° C. and then slowly cooled to 55° C., after which 40 units of Bst XI (at 10 units/µl) was added to bring the reaction volume to 60 µl. The mixture was incubated at 55° C. for 2 hours after which the beads were washed three times in TE (pH 8.0).

The segment of pGEM7Z to be attached to the beads was prepared as follows: Two PCR primers (SEQ ID NO: 31 and SEQ ID NO: 32) were prepared using standard protocols:

| Primer 1: | 5'-CTAAACCATTGGTATGGGCCAGTGAATTGTAATA |
|---|---|
| Primer 2: | 5'-CGCGCAGCCCGCATCGTTTATGCTACAGACTGTC-AGTGCAGCTCTCCGATCCAAA |

The PCR reaction mixture consisted of the following: 1 µl pGEM7Z at 1 ng/µl; 10 µl primer 1 at 10 pmol/µl; 10 µl primer 2 at 10 pmol/µl; 10 µl deoxyribonucleotide triphosphates at 2.5 mM; 10 µl 10×PCR buffer (Perkin-Elmer); 0.5 µl Taq DNA polymerase at 5 units/µl; and 58 µl distilled water to give a final volume of 100 µl. The reaction mixture was subjected to 25 cycles of 93° C. for 30 sec; 60° C. for 15 sec; and 72° C for 60 sec, to give a 172 basepair product, which was successively digested with Bbv I (100 µl PCR reaction mixture, 12 µl 10×#1 New England Biolabs buffer, 8 µl Bbv I at 1 unit/µl incubate at 37° C. for 6 hours) and with Bst XI (to the Bbv I reaction mixture was added: 5 µl 1M NaCl, 67 µl distilled water, and 8 µl Bst XI at 10 units/µl, and the resulting mixture was incubated at 55° C. for 2 hours).

After passing the above reaction mixture through a Centricon 30 (Amicon, Inc.) spin column following manufacturer's protocol, the Bbv I/Bst XI-restricted fragment was ligated to the double stranded linker attached to the Ballotini beads in the following mixture: 17 µl Bbv I/Bst XI-restricted fragment (10 µg), 10 µl beads (20 mg), 6 ml 10×ligation buffer (New England Biolabs, referred to below as NEB), 5 µl T4 DNA ligase at 2000 units/µl, and 22 µl distilled water, which mixture was incubated at 25° C. for 4 hours, after which the beads were washed 3 times with TE (pH 8.0), leaving the following target polynucleotide for sequencing:

```
              ... TCTGTAGCT
[BEAD] --  ...  AGACATCGAATTT-5'
```

The strands of the following probes (24 nucleotides in labeled strand and 18 nucleotides in non-labeled strand) were separately synthesized on an automated DNA synthesizer (model 392 Applied Biosystems, Foster City) using standard methods:

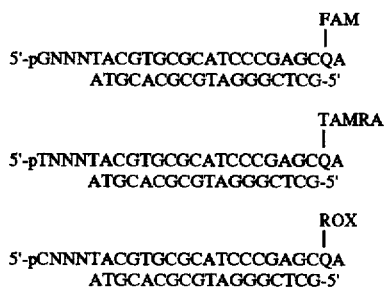

-continued

```
           JOE
            |
5'-pANNNTACGTGCGCATCCCGAGCQA
    ATGCACGCGTAGGGCTCG-5'
``` where p is a monophosphate, N indicates A, C, G, or T, Q is a branched linker carrying a protected amino group for attachment of a label (e.g. Uni-Link AminoModifier, available from Clontech Laboratories, Palo Alto, Calif.), and FAM, TAMRA, ROX, and JOE are as defined above. $5.0 \times 10^4$ pmol of each probe was combined in TE to form a mixture at a concentration of 1000 pmol/μl.

Ligations were carried out in a mixture consisting of 5 μl beads (20 mg), 3 μl NEB 10×ligase buffer, 5 μl probe mix, 2.5 μl NEB T4 DNA ligase (2000 units/μl), and 14.5 μl distilled water. The mixture was incubated at 16° C. for 30 minutes, after which the beads were washed 3 times in TE (pH 8.0). Cleavages were carried out in a mixture consisting of 5 μl beads (20 mg), 3 μl 10×NEB buffer #3, 3 μl NEB Fok I (4 units/μl), and 19 μl distilled water. The mixture was incubated at 37° C. for 30 minutes, after which the beads were washed 3 times in TE (pH 8.0).

After each ligation, a sample of the beads with the ligated complex was removed for size analysis on a model 373 DNA sequencer using 672 GeneScan software (Applied Biosystems). The readout of the system provides a different colored curve for fragments labeled with the four different dyes (black for TAMRA, blue for FAM, green for JOE, and red for ROX). A 6% denaturing (8M urea) polyacrylamide gel was employed in accordance with manufacturer's protocols. About 0.5 mg of beads were placed in 4 μl of formamide loading buffer in accordance with the manufacturer's protocol for analyzing sequencing fragments. Samples were heated to 95° C. for 2 min then cooled by placing on ice, after which the entire sample was loaded into one lane.

Figure 4A:
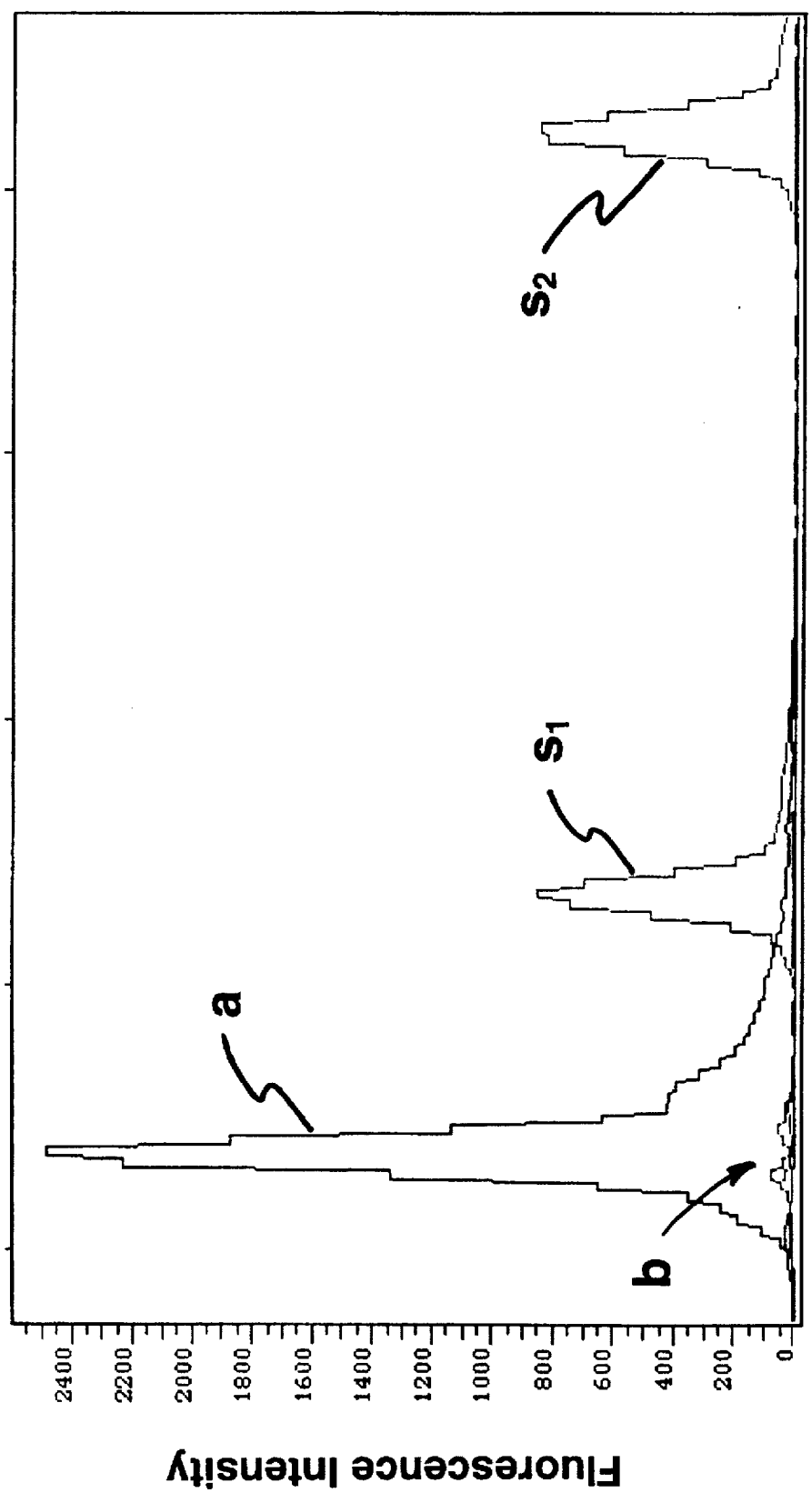
FIGS. 4a through 4d illustrate data showing the fidelity of nucleotide identification through ligation with a ligase.
Figure 4B:
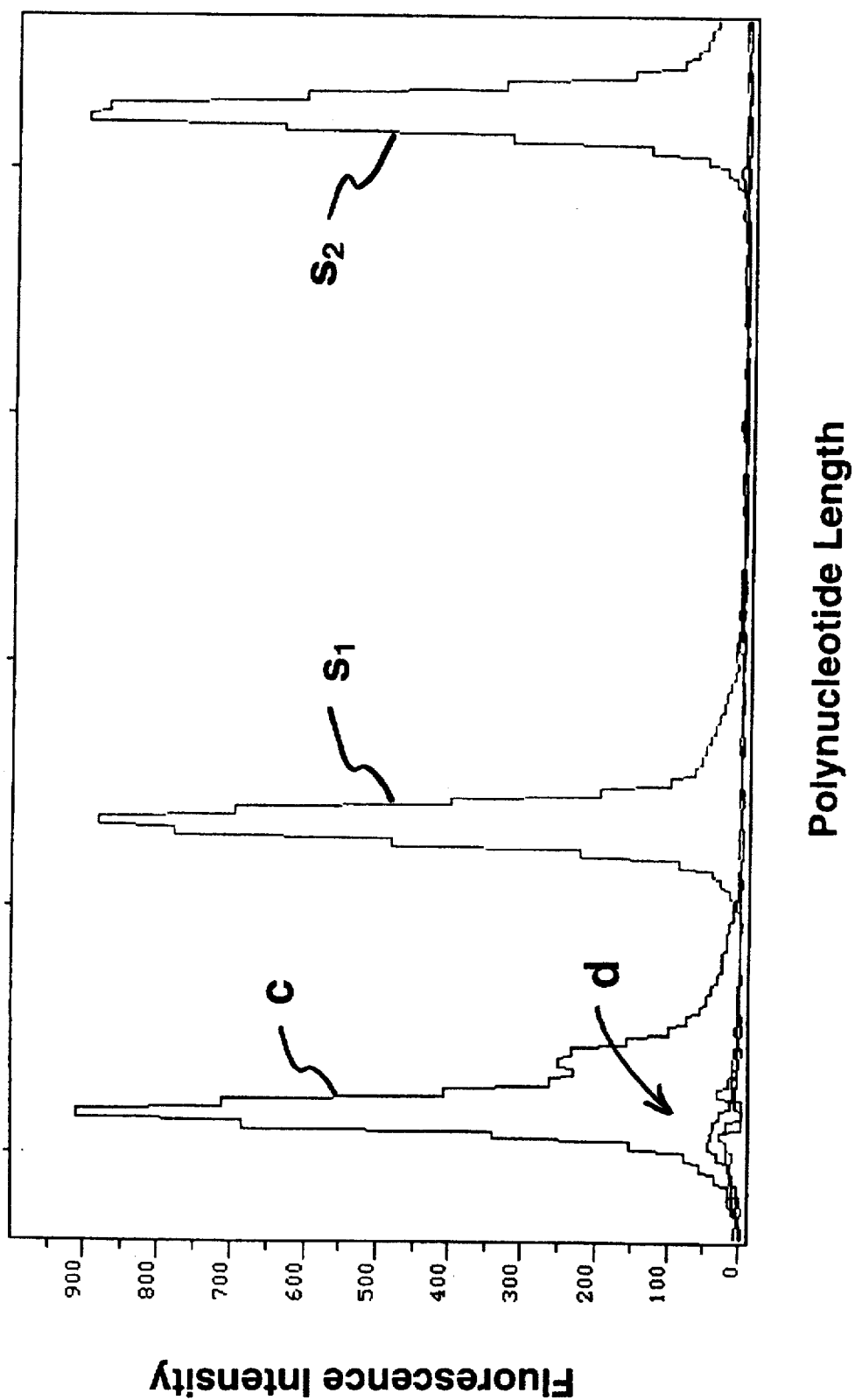
Figure 4C:
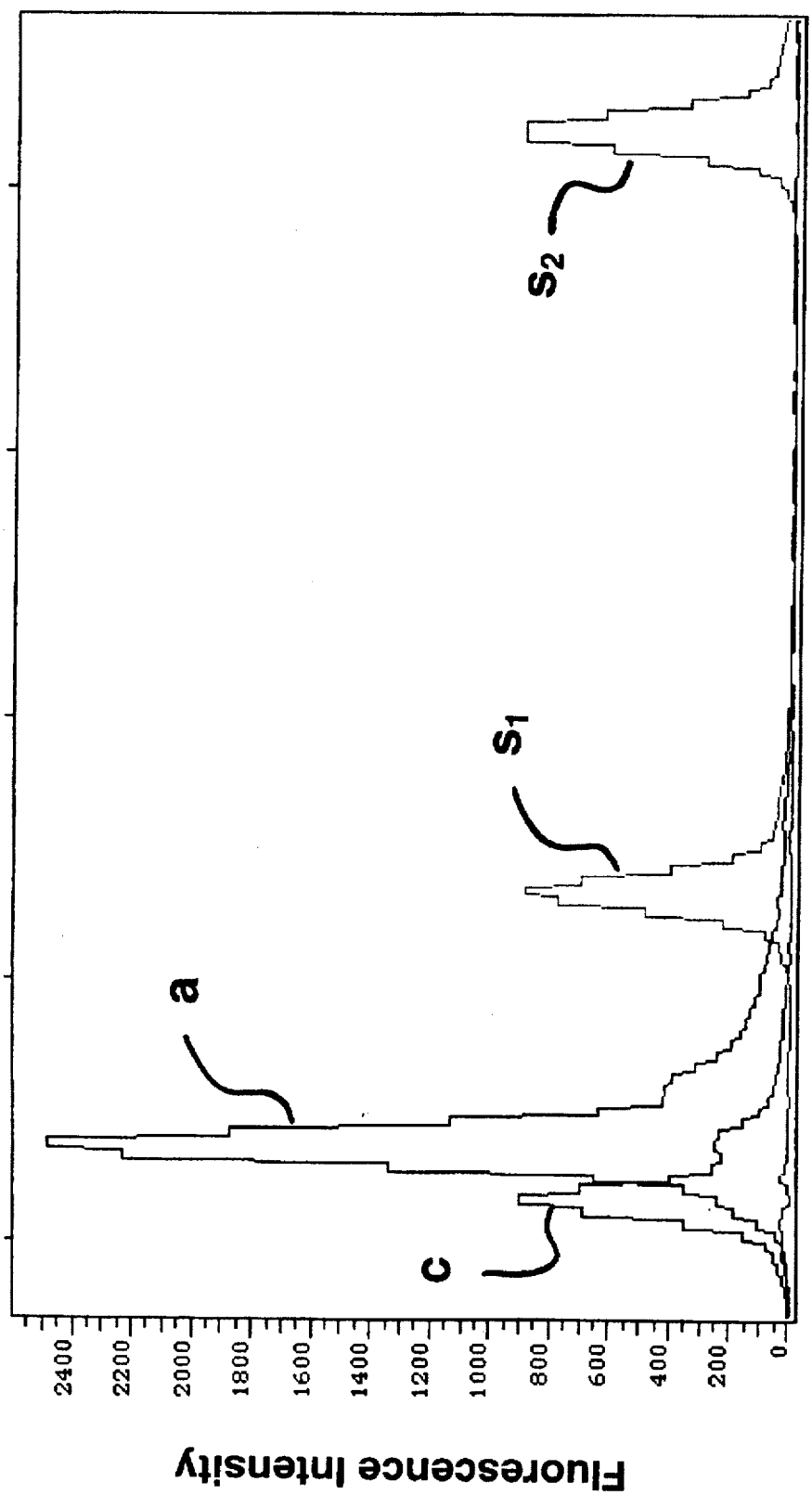
Figure 4D:
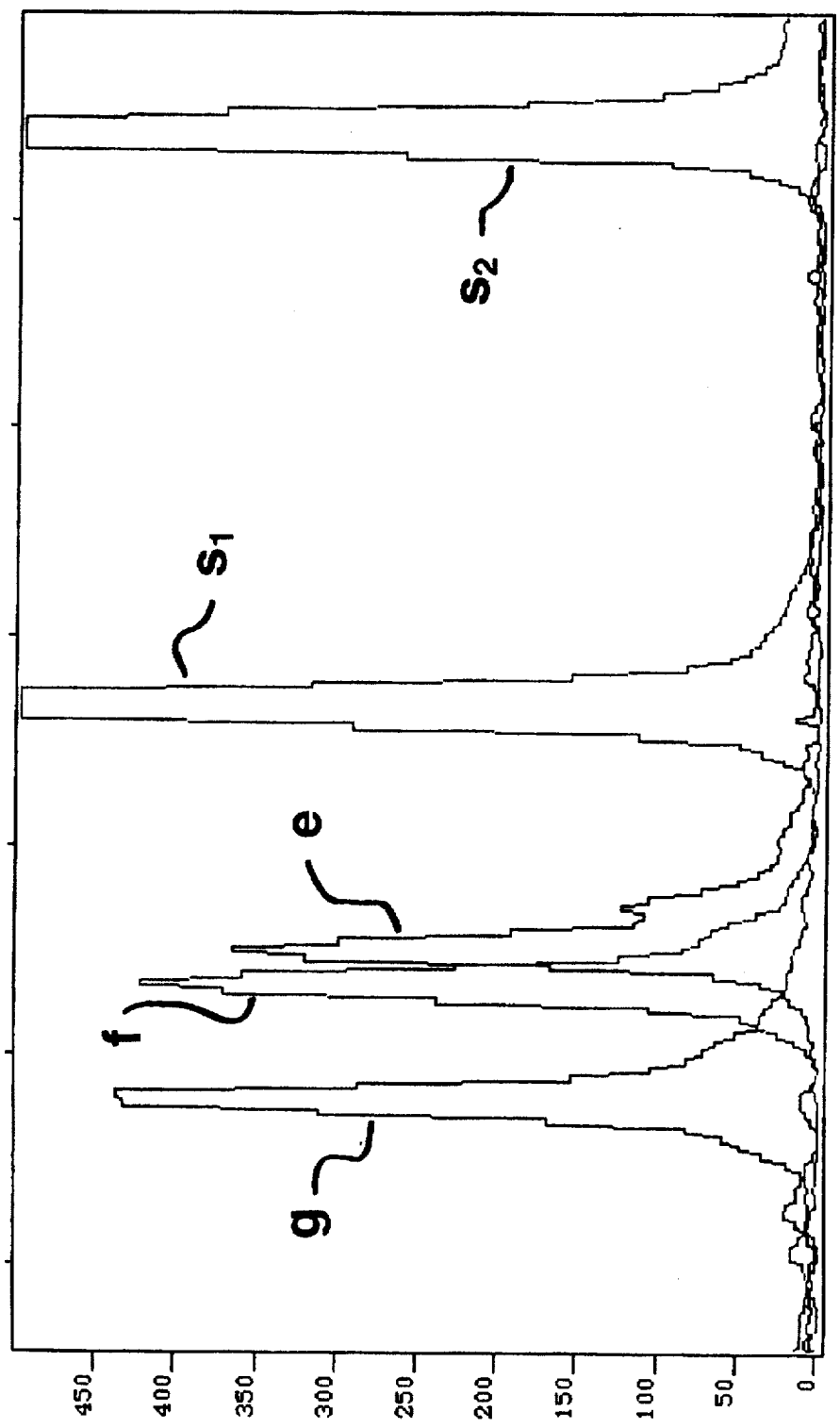

Results of four cycles of ligation are shown in FIGS. 4a through 4d. Curve a of FIG. 4a demonstrates that the first nucleotide in the target sequence is correctly identified as A. The first nucleotide is the one in the protruding strand closest to the double stranded portion of the target polynucleotide. Curves $s_1$ and $s_2$ are 172 and 186 nucleotide size standards. The very low curves indicated by "b" in the figure show that the fidelity of the ligase was very high, in that little or no other probes besides the correct one were ligated. Curve c in FIG. 4b demonstrates that the second nucleotide of the target polynucleotide is correctly identified as A. Note that as in FIG. 4a, only an insignificant number probes were incorrectly ligated, as indicated by "d". FIG. 4c is a superposition of curve c of FIG. 4b onto the curve of FIG. 4a. This shows that curve c corresponds to a fragment one nucleotide shorter than that of curve a, as expected after the Fok I digestion. FIG. 4d is a superposition of the data on the fragments generated in cycles 2, 3, and 4, indicated by curves e, f, and g, respectively. Again, the fidelity of ligation is very high and the peaks of the curves are in the correct order, as expected from the one nucleotide size reduction that takes place after each Fok I digestion.

EXAMPLE 7

Sequencing a Target Polynucleotide Amplified from pGEM7Z: Identification of Nucleotides by a Polymerase Extension Reaction In this example, a segment of plasmid pGEM7Z was amplified by PCR using a biotinylated primer and attached by the biotin to strepavidinated magnetic beads. After each cleave step, the resulting protruding strand of the target polynucleotide was used as a template to extend the recessed strand by one nucleotide using a DNA polymerase in the presence of a mixture of labeled dideoxynucleoside triphosphates. The extended strand was then analyzed by gel electrophoresis as described above. The PCR reaction was prepared by combining the following: 1 μl pGEM7Z plasmid (1 pg/μl), 1 μl B002 biotinylated primer (100 pmoles/μl), 1 μl -337 primer (100 pmole/μl), 20 μl 10 nucleoside triphosphates (2.5 mM stock of each triphosphate), 20 μl 10×Taq buffer (Perkin-Elmer), 156 μl distilled water, and 1 μl Taq (2 units/ml). The primers had the following sequences:

B002: (SEQ ID NO: 39) 5'-biotin-CCCGACGTCGCATGCTC-CTCTA

-337: (SEQ ID NO: 40) 5'-GCGCGTTGGCCGATTCATTA

The above PCR mixture was cycled 25 times through the following temperatures in a Perkin-Elmer 9600 thermal cycler: 94° C. 1 min, 52° C. 1 min, and 72° C. 2 min. After cycling, to the reaction mixture was added 10 μg glycogen and 100 μl chloroform, after which the aqueous phase was removed and combined with 20 μl 3M NaOAc and 500 μl ethanol. After the resulting mixture was spun in a microfuge for 30 min, the precipitate was collected, dried, and resuspended in 50 μl $H_2O$. Prior to combining with the biotinylated DNA, the strepavidinated magnetic beads (20 μl) were washed 3 times with 100 μl of 2×bead wash (1.0M NaCl, Tris, triton X-100) and then resuspended in 10 μl of 2×bead wash. 10 ml of the biotinylated DNA solution was added to the beads and allowed to sit for 5 min with agitation, after which the beads were magnetically pulled to the side of the tube, the supernatant removed, and the beads washed twice with 2×bead wash and 3 time with water.

An initial protruding strand was produced at the end of the attached target polynucleotide by cleaving with Fok I as follows: To the beads were added: 44 μl $H_2O$, 5 μl 10×Fok I buffer (New England Biolabs), and 1 μl Fok I (New England Biolabs, 4 units/μl). The mixture was incubated for 30 min, after which the supernatant was removed from the magnetic beads. After this initial cleavage, three cycles of extension, ligation, excision, and cleavage were carried out with the following protocols. After each extension a sample of beads were removed from the reaction mixture and the labeled strand of the target polynucleotide was analyzed as described in Example 6.

Extension reactions were carried out with Sequenase DNA polymerase in the presence of labeled dideoxynucleosides by adding to the beads the following mixture: 17.0 μl $H_2O$, 5.0 5×Sequenase buffer, 2.5 μl 10×Taq fluorescent dye-labeled terminators (Perkin-Elmer), and 1.0 μl Sequenase 2.0 (13 units/μl). After incubation at 37° C. for 15 min, proteinaceous material was extracted with 50 μl phenol/chloroform, which was then back extracted with 25 μl $H_2O$. The combined aqueous phases were again extracted with 50 μl chloroform, after which the aqueous phase was removed and mixed with 5 μl 3M NaOAc and 125 μl ethanol. The precipitate was collected, microfuged for 15 min, washed with 70% ethanol, and dried.

A mixed probe was prepared as described in Example 6 with the following differences: (i) the probe is unlabeled, thus, only a single mixture need be prepared; and (ii) the protruding strand consisted of three nucleotides such that each of the three positions in the protruding strand could be A, C, G, or T, i.e. each was "N" as described above. Ligation was carried out as follows: To a 0.5 ml tube containing the dried DNA was added 20.5 μl probe (100 pmoles/μl), 2.5 μl 10×ligase buffer (New England Biolabs), 2.0 μl ligase (New England Biolabs, 0.4 units/μl . The mixture was incubated for 1 hour at 16° C., after which the DNA was purified on a spin column prepared as follows: resin was swelled with 800 μl $H_2O$ for 45 min, drained, and spun at 800 rpm for 2 min.

The labeled terminator was excised from the ligated complex with the 3'→5' exonuclease activity of Deep Vent DNA polymerase. At the same time, the polymerase extends the strand the length of the probe, thereby repairing the nick caused by the presence of the dideoxy terminator. The reaction was carried out in a MicroAmp tube (Perkin-Elmer) containing the following: 25.0 µl DNA, 3.5 µl 10×nucleoside triphosphates (1.25 mM each), 3.5 µl 1×Vent buffer (New England Biolabs), and 2.0 µl Deep Vent DNA polymerase (2 units/µl). The mixture was incubated for 60 min at 80° C. under oil, after which 15 ml H$_2$O was added and the combined mixture was extracted with 100 µl chloroform. The aqueous phase was removed and mixed with 5 µl 3M NaOAc and 125 µl ethanol, after which the precipitate was collected, microfuged for 15 min, washed with 70% ethanol, and dried.

Fok I cleavage was carried out by resuspending the DNA in 21.5 µl H$_2$O and adding 2.5 µl 10×Fok I buffer (New England Biolabs) and 1.0 µl Fok I (4 units/ml). The mixture was incubated for 15 min at 37° C., after which the DNA was purified on a spin column prepared as described above.

Figure 5A:
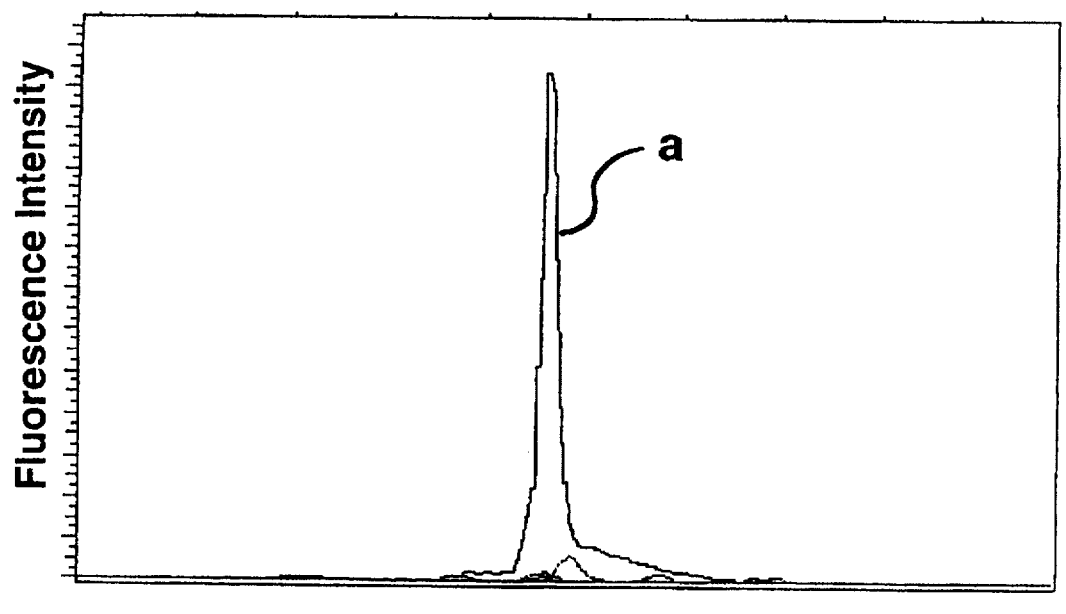
FIGS. 5a through 5c illustrate data showing nucleotide identification through polymerase extension.
Figure 5B:
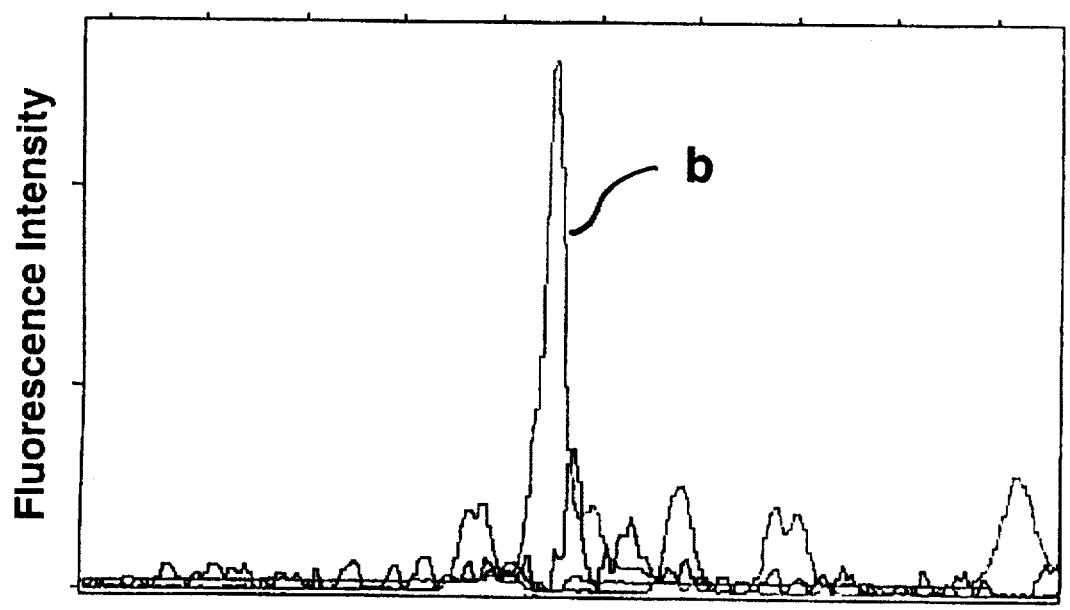
Figure 5C:
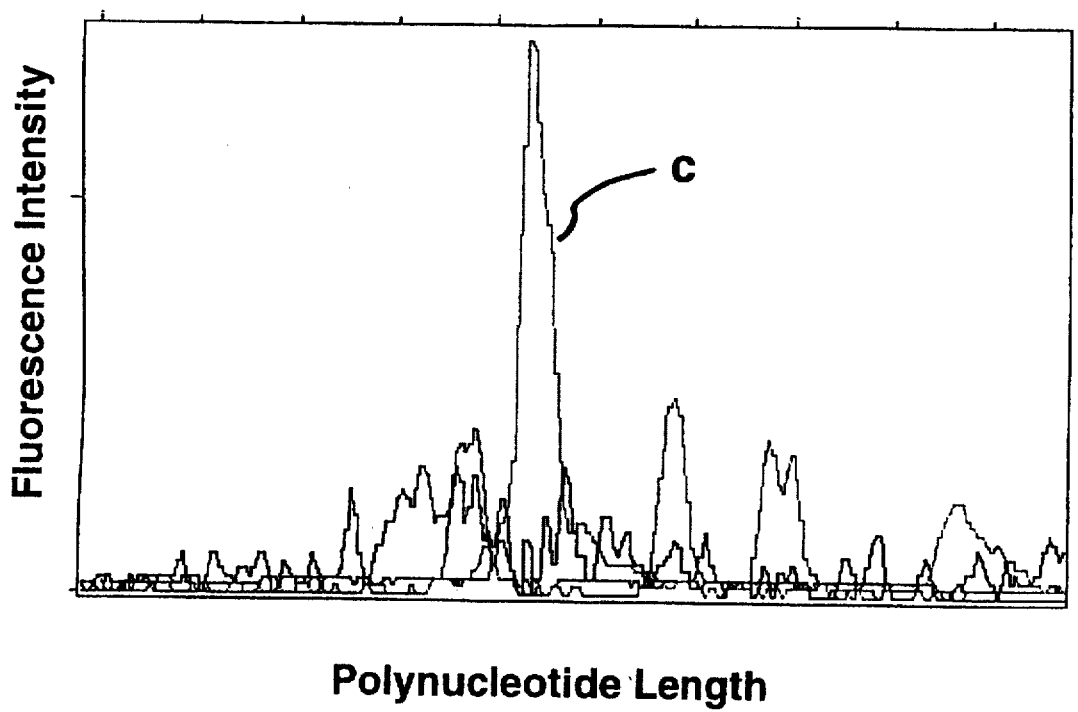

Results are shown in FIGS. 5a through 5c. The colors of the curves generated by the GeneScan software containing the dominant peaks in the figures corresponded to the correct nucleotide in the target polynucleotide.

---

We claim:

1. A method for determining a nucleotide sequence of a polynucleotide, the method comprising the steps of:
   (a) ligating a probe to an end of a polynucleotide, the probe having a nuclease recognition site of a nuclease whose cleavage site is separate from its recognition site, and the polynucleotide having been replicated in the presence of 5-methydeoxylcytidine triphosphate;
   (b) identifying one or more nucleotides at the end of the polynucleotide by the identity of the probe ligated thereto or by extending a strand of the polynucleotide or probe;
   (c) cleaving the polynucleotide with a nuclease recognizing the nuclease recognition site of the probe such that the polynucleotide is shortened by one or more nucleotides; and
   (d) repeating said steps (a) through (c) until said nucleotide sequence of the polynucleotide is determined.

2. The method of claim 1 wherein said nuclease is a type IIs restriction endonuclease.

3. The method of claim 2 wherein said step of ligating includes treating said polynucleotide and said probe with a ligase.

4. The method of claim 3 wherein said polynucleotide has a protruding strand at at least one end and said probe has a protruding strand at at least one end, and wherein said step of ligating includes providing said probe as a mixture such that the protruding strand of said probe includes every possible sequence of nucleotides the length of the protruding strand.

5. The method of claim 4 wherein said protruding strand of said polynucleotide has a 5'-phosphoryl group and wherein said complementary protruding strand of said probe lacks a 5'-phosphoryl group.

6. The method of claim 5 wherein said step of ligating includes treating said polynucleotide and said probe in succession with (i) a ligase to ligate said protruding strand having said 5'-phosphoryl group to said probe, (ii) a kinase to phosphorylate said complementary protruding strand of said probe, and (iii) a ligase to ligate said complementary protruding strand of said probe to said polynucleotide.

7. The method of claim 4 further including the step of removing unligated probe from said polynucleotide after said step of ligating.

8. The method of claim 4 wherein said step of identifying includes identifying a first nucleotide in said protruding strand of said polynucleotide by the identity of said probe ligated thereto and identifying a second nucleotide in said protruding strand of said polynucleotide by extending a strand of said probe.

9. The method of claim 4 further including a step of capping said polynucleotide which fails to ligate to said probe.

10. The method of claim 9 wherein said step of capping includes extending said polynucleotide with a DNA polymerase in the presence of chain-terminating nucleoside triphosphates.

11. The method of claim 4 further including a step of capping said probe which fails to be cleaved from said polynucleotide.

12. The method of claim 11 wherein said step of capping includes treating said probe with a methylase.

13. The method of claim 11 wherein said step of capping includes providing said probe with a second nuclease recognition site and cleaving said probe with a second nuclease which recognizes the second recognition site such that said polynucleotide is rendered incapable of being ligated to said probe in a subsequent ligation step.

14. A method for determining a nucleotide sequence of a polynucleotide, the method comprising the steps of:
   (a) ligating a probe to an end of a polynucleotide, the probe having a nuclease recognition site of a nuclease whose cleavage site is separate from its recognition site;
   (b) identifying a plurality of nucleotides at the end of the polynucleotide by the identity of the probe ligated thereto or by extending a strand of the polynucleotide or probe;
   (c) cleaving the polynucleotide with a nuclease recognizing the nuclease recognition site of the probe such that the polynucleotide is shortened by one or more nucleotides; and
   (d) repeating said steps (a) through (c) until said nucleotide sequence of the polynucleotide is determined.

15. The method of claim 14 wherein said nuclease is a type IIs restriction endonuclease.

16. The method of claim 15 wherein said step of ligating includes treating said polynucleotide and said probe with a ligase.

17. The method of claim 16 wherein said polynucleotide has a protruding strand at at least one end and said probe has a protruding strand at at least one end, and wherein said step of ligating includes providing said probe as a mixture such that the protruding strand of said probe includes every possible sequence of nucleotides the length of the protruding strand.

18. The method of claim 17 wherein said protruding strand of said polynucleotide has a 5'-phosphoryl group and wherein said complementary protruding strand of said probe lacks a 5'-phosphoryl group.

19. The method of claim 18 wherein said step of ligating includes treating said polynucleotide and said probe in succession with (i) a ligase to ligate said protruding strand having said 5'-phosphoryl group to said probe, (ii) a kinase to phosphorylate said complementary protruding strand of said probe, and (iii) a ligase to ligate said complementary protruding strand of said probe to said polynucleotide.

20. The method of claim 17 further including the step of removing unligated probe from said polynucleotide after said step of ligating.

21. The method of claim 17 wherein said step of identifying includes identifying a first nucleotide in said protruding strand of said polynucleotide by the identity of said probe ligated thereto and identifying a second nucleotide in said protruding strand of said polynucleotide by extending a strand of said probe.

22. The method of claim 17 further including a step of capping said polynucleotide which fails to ligate to said probe.

23. The method of claim 22 wherein said step of capping includes extending said polynucleotide with a DNA polymerase in the presence of chain-terminating nucleoside triphosphates.

24. The method of claim 17 further including a step of capping said probe which fails to be cleaved from said polynucleotide.

25. The method of claim 24 wherein said step of capping includes treating said probe with a methylase.

26. The method of claim 24 wherein said step of capping includes providing said probe with a second nuclease recognition site and cleaving said probe with a second nuclease which recognizes the second recognition site such that said polynucleotide is rendered incapable of being ligated to said probe in a subsequent ligation step.

27. The method of claim 17 wherein said plurality is two.

28. The method of claim 27 wherein said protruding strands of said polynucleotide and said probe each have a length of two nucleotides.

* * * * *